US008845649B2

(12) United States Patent
Jackson

(10) Patent No.: US 8,845,649 B2
(45) Date of Patent: *Sep. 30, 2014

(54) SPINAL FIXATION TOOL SET AND METHOD FOR ROD REDUCTION AND FASTENER INSERTION

(76) Inventor: Roger P. Jackson, Prairie Village, KS (US)

( * ) Notice: Subject to any disclaimer, the term of this patent is extended or adjusted under 35 U.S.C. 154(b) by 884 days.

This patent is subject to a terminal disclaimer.

(21) Appl. No.: 12/454,132

(22) Filed: May 13, 2009

(65) Prior Publication Data

US 2009/0228055 A1    Sep. 10, 2009

Related U.S. Application Data

(63) Continuation of application No. 10/950,377, filed on Sep. 24, 2004, now Pat. No. 7,651,502.

(51) Int. Cl.
| *A61B 17/60* | (2006.01) |
| *A61F 2/00* | (2006.01) |
| *A61B 17/70* | (2006.01) |
| *A61B 19/00* | (2006.01) |

(52) U.S. Cl.
CPC ......... *A61B 17/7086* (2013.01); *A61B 17/7091* (2013.01); *A61B 2019/307* (2013.01)
USPC .......................................................... 606/99

(58) Field of Classification Search
USPC ................... 606/99, 104, 264–267, 270–273; 81/57.37, 177.4, 490
See application file for complete search history.

(56) References Cited

U.S. PATENT DOCUMENTS

| 854,956 A | 5/1907 | Martin |
| 1,472,464 A | 10/1923 | Ellison |

(Continued)

FOREIGN PATENT DOCUMENTS

| CA | 2577436 | 6/2006 |
| DE | 4239716 | 8/1994 |

(Continued)

OTHER PUBLICATIONS

Brochure of Spinal Concepts, InCompass, Thoracolumbar Fixation System, Publication Date: Oct. 2003.

(Continued)

*Primary Examiner* — Anu Ramana
(74) *Attorney, Agent, or Firm* — John C. McMahon

(57) ABSTRACT

A tool for implantation of a rod into a bone screw implanted in a human spine includes a guide member having a laterally opening channel disposed along an entire length thereof for side loading and receiving an implant fastener. A rod pushing member and a handle with a laterally opening channel are coaxial with the guide member, with the rod pushing member being rotatingly mateable to the guide member and the handle having a spring attachment mechanism for attaching the handle to the guide member. The guide member includes spring tabs for attachment to a bone screw, the tabs biased away from the bone screw. The rod pushing member includes a sleeve that extends substantially about the guide member, pressing the spring tabs toward the bone screw and into apertures on the bone screw arms. The rod pushing member sleeve also operatively functions as a rod pusher that abuts a rod as the sleeve is translated along the guide member and toward the bone screw. The handle lateral opening receives and supports a manipulation tool for inserting and installing an implant fastener for attaching the rod to the bone screw.

42 Claims, 8 Drawing Sheets

(56) References Cited

U.S. PATENT DOCUMENTS

| | | |
|---|---|---|
| 2,243,717 A | 5/1941 | Moreira |
| 2,346,346 A | 4/1944 | Anderson |
| 2,362,999 A | 11/1944 | Elmer |
| 2,524,095 A | 10/1950 | Williams |
| 2,531,892 A | 11/1950 | Reese |
| 2,532,972 A | 12/1950 | Vertin |
| 2,579,438 A | 12/1951 | Longfellow |
| 2,669,896 A | 2/1954 | Cough |
| 2,813,450 A | 11/1957 | Dzus |
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |
| 3,997,138 A | 12/1976 | Crock et al. |
| 4,033,139 A | 7/1977 | Frederick |
| 4,041,939 A | 8/1977 | Hall |
| 4,190,091 A | 2/1980 | Colognori |
| 4,347,845 A | 9/1982 | Mayfield |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,838,264 A | 6/1989 | Bremer et al. |
| 4,877,020 A | 10/1989 | Vich |
| 4,887,596 A | 12/1989 | Sherman |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,015,247 A | 5/1991 | Michelson |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,067,955 A | 11/1991 | Cotrel |
| 5,084,048 A | 1/1992 | Jacob et al. |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,862 A | 2/1994 | Baker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,409,489 A | 4/1995 | Sioufi |
| 5,413,661 A | 5/1995 | Spengler et al. |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,830 A | 7/1998 | Farris |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,817,094 A | 10/1998 | Errico et al. |

(56) References Cited

U.S. PATENT DOCUMENTS

| | | | |
|---|---|---|---|
| 5,855,151 A * | 1/1999 | Habermehl | 81/434 |
| 5,863,293 A | 1/1999 | Richelsoph | |
| 5,865,487 A | 2/1999 | Gore et al. | |
| 5,873,878 A | 2/1999 | Harms et al. | |
| 5,876,402 A | 3/1999 | Errico et al. | |
| 5,879,350 A | 3/1999 | Sherman et al. | |
| 5,879,351 A | 3/1999 | Viart | |
| 5,882,350 A | 3/1999 | Ralph et al. | |
| 5,885,286 A | 3/1999 | Sherman et al. | |
| 5,891,145 A | 4/1999 | Morrison et al. | |
| 5,902,231 A | 5/1999 | Foley et al. | |
| RE36,221 E | 6/1999 | Breard et al. | |
| 5,910,141 A | 6/1999 | Morrison et al. | |
| 5,938,663 A | 8/1999 | Petreto | |
| 5,943,926 A * | 8/1999 | Habermehl | 81/434 |
| 5,944,465 A | 8/1999 | Janitzki | |
| 5,951,553 A | 9/1999 | Betz | |
| 5,954,725 A | 9/1999 | Sherman et al. | |
| 5,961,517 A | 10/1999 | Biedermann et al. | |
| 5,964,760 A | 10/1999 | Richelsoph | |
| 6,001,098 A | 12/1999 | Metz-Stavenhagen et al. | |
| 6,004,349 A | 12/1999 | Jackson | |
| 6,010,503 A | 1/2000 | Richelsoph et al. | |
| 6,019,759 A | 2/2000 | Rogozinski | |
| 6,022,350 A | 2/2000 | Ganem | |
| 6,053,917 A | 4/2000 | Sherman et al. | |
| 6,059,786 A | 5/2000 | Jackson | |
| 6,063,088 A | 5/2000 | Winslow | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,086,588 A | 7/2000 | Ameil et al. | |
| 6,090,110 A | 7/2000 | Metz-Stavenhagen | |
| 6,090,111 A | 7/2000 | Nichols | |
| 6,099,528 A | 8/2000 | Saurat | |
| 6,102,912 A | 8/2000 | Cazin et al. | |
| 6,102,913 A | 8/2000 | Jackson | |
| 6,110,172 A | 8/2000 | Jackson | |
| 6,113,601 A | 9/2000 | Tatar | |
| 6,117,137 A | 9/2000 | Halm et al. | |
| 6,132,431 A | 10/2000 | Nilsson et al. | |
| 6,132,432 A | 10/2000 | Richelsoph | |
| 6,132,434 A | 10/2000 | Sherman et al. | |
| 6,136,002 A | 10/2000 | Shih et al. | |
| 6,139,549 A | 10/2000 | Keller | |
| 6,143,032 A | 11/2000 | Schafer et al. | |
| 6,146,383 A | 11/2000 | Studer et al. | |
| 6,164,170 A * | 12/2000 | Habermehl et al. | 81/434 |
| 6,183,472 B1 | 2/2001 | Lutz | |
| 6,186,718 B1 | 2/2001 | Fogard | |
| 6,187,005 B1 | 2/2001 | Brace et al. | |
| 6,189,422 B1 | 2/2001 | Stihl | |
| 6,193,720 B1 | 2/2001 | Yuan et al. | |
| 6,214,012 B1 | 4/2001 | Karpman et al. | |
| RE37,161 E | 5/2001 | Michelson et al. | |
| 6,224,596 B1 | 5/2001 | Jackson | |
| 6,224,598 B1 | 5/2001 | Jackson | |
| 6,235,028 B1 | 5/2001 | Brumfield et al. | |
| 6,235,034 B1 | 5/2001 | Bray | |
| 6,241,730 B1 | 6/2001 | Alby | |
| 6,248,105 B1 | 6/2001 | Schlapfer et al. | |
| 6,248,107 B1 | 6/2001 | Foley et al. | |
| 6,251,112 B1 | 6/2001 | Jackson | |
| 6,254,146 B1 | 7/2001 | Church | |
| 6,254,602 B1 | 7/2001 | Justis | |
| 6,267,764 B1 | 7/2001 | Elberg | |
| 6,267,765 B1 | 7/2001 | Taylor et al. | |
| 6,273,888 B1 | 8/2001 | Justis | |
| 6,277,122 B1 | 8/2001 | McGahan et al. | |
| 6,280,442 B1 | 8/2001 | Barker et al. | |
| 6,280,445 B1 | 8/2001 | Morrison et al. | |
| 6,287,308 B1 | 9/2001 | Betz et al. | |
| 6,287,311 B1 | 9/2001 | Sherman et al. | |
| 6,290,700 B1 | 9/2001 | Schmotzer | |
| 6,296,642 B1 | 10/2001 | Morrison et al. | |
| 6,296,643 B1 | 10/2001 | Hopf et al. | |
| 6,299,613 B1 | 10/2001 | Ogilvie et al. | |
| 6,299,616 B1 | 10/2001 | Berger | |
| 6,302,888 B1 | 10/2001 | Mellinger et al. | |
| 6,309,391 B1 | 10/2001 | Crandall et al. | |
| 6,315,564 B1 | 11/2001 | Levisman | |
| 6,315,779 B1 | 11/2001 | Morrison et al. | |
| 6,331,179 B1 | 12/2001 | Freid et al. | |
| 6,355,040 B1 | 3/2002 | Richelsoph et al. | |
| RE37,665 E | 4/2002 | Ralph et al. | |
| 6,368,321 B1 | 4/2002 | Jackson | |
| 6,371,957 B1 | 4/2002 | Amrein et al. | |
| 6,379,356 B1 | 4/2002 | Jackson | |
| 6,402,752 B2 | 6/2002 | Schaffler-Wachter et al. | |
| 6,402,757 B1 | 6/2002 | Moore et al. | |
| 6,440,133 B1 | 8/2002 | Beale et al. | |
| 6,440,137 B1 | 8/2002 | Horvath et al. | |
| 6,443,956 B1 | 9/2002 | Ray | |
| 6,451,021 B1 | 9/2002 | Ralph et al. | |
| 6,471,703 B1 | 10/2002 | Ashman | |
| 6,471,705 B1 | 10/2002 | Biedermann et al. | |
| 6,478,798 B1 | 11/2002 | Howland | |
| 6,478,800 B1 | 11/2002 | Fraser et al. | |
| 6,478,801 B1 | 11/2002 | Ralph et al. | |
| 6,485,491 B1 | 11/2002 | Farris et al. | |
| 6,485,492 B1 | 11/2002 | Halm et al. | |
| 6,485,494 B1 | 11/2002 | Haider | |
| 6,488,681 B2 | 12/2002 | Martin et al. | |
| 6,508,818 B2 | 1/2003 | Steiner et al. | |
| 6,511,484 B2 | 1/2003 | Torode et al. | |
| 6,520,962 B1 | 2/2003 | Taylor et al. | |
| 6,527,804 B1 | 3/2003 | Gauchet et al. | |
| 6,530,929 B1 | 3/2003 | Justis et al. | |
| 6,533,786 B1 | 3/2003 | Needham et al. | |
| 6,539,826 B2 | 4/2003 | Oesterle et al. | |
| 6,540,749 B2 | 4/2003 | Schafer et al. | |
| 6,547,790 B2 | 4/2003 | Harkey, III et al. | |
| 6,551,320 B2 | 4/2003 | Liebermann | |
| 6,551,323 B2 | 4/2003 | Doubler et al. | |
| 6,554,831 B1 | 4/2003 | Rivard et al. | |
| 6,554,832 B2 | 4/2003 | Shluzas | |
| 6,554,834 B1 | 4/2003 | Crozet et al. | |
| 6,558,387 B2 | 5/2003 | Errico et al. | |
| 6,562,038 B1 | 5/2003 | Morrison | |
| 6,562,040 B1 | 5/2003 | Wagner | |
| 6,565,565 B1 | 5/2003 | Yuan et al. | |
| 6,565,567 B1 | 5/2003 | Haider | |
| 6,572,618 B1 | 6/2003 | Morrison | |
| 6,582,436 B2 | 6/2003 | Schlapfer et al. | |
| 6,582,466 B1 | 6/2003 | Gauchet | |
| 6,585,740 B2 | 7/2003 | Schlapfer et al. | |
| 6,595,992 B1 | 7/2003 | Wagner et al. | |
| 6,595,993 B2 | 7/2003 | Donno et al. | |
| 6,599,294 B2 | 7/2003 | Fuss et al. | |
| 6,602,255 B1 | 8/2003 | Campbell et al. | |
| 6,610,063 B2 | 8/2003 | Kumar et al. | |
| 6,613,050 B2 | 9/2003 | Wagner et al. | |
| 6,616,667 B1 | 9/2003 | Steiger et al. | |
| 6,616,669 B2 | 9/2003 | Ogilvie | |
| 6,623,484 B2 | 9/2003 | Betz | |
| 6,623,485 B2 | 9/2003 | Doubler et al. | |
| 6,626,347 B2 | 9/2003 | Ng | |
| 6,626,907 B2 | 9/2003 | Campbell et al. | |
| 6,626,908 B2 | 9/2003 | Cooper et al. | |
| 6,635,059 B2 | 10/2003 | Randall et al. | |
| 6,635,060 B2 | 10/2003 | Hanson et al. | |
| 6,648,885 B1 | 11/2003 | Friesem | |
| 6,648,887 B2 | 11/2003 | Ashman | |
| 6,648,888 B1 | 11/2003 | Shluzas | |
| 6,652,526 B1 | 11/2003 | Arafiles | |
| 6,652,765 B1 | 11/2003 | Beaty | |
| 6,656,179 B1 | 12/2003 | Schaefer et al. | |
| 6,656,181 B2 | 12/2003 | Dixon et al. | |
| 6,660,004 B2 | 12/2003 | Barker et al. | |
| 6,660,006 B2 | 12/2003 | Markworth et al. | |
| 6,663,632 B1 | 12/2003 | Frigg | |
| 6,663,635 B2 | 12/2003 | Frigg et al. | |
| 6,673,073 B1 | 1/2004 | Schafer | |
| 6,676,661 B1 | 1/2004 | Martin Benlloch et al. | |

(56) References Cited

U.S. PATENT DOCUMENTS

| | | |
|---|---|---|
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,248 B2 | 3/2004 | Jackson |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,687 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Bieeermann et al. |
| 6,740,086 B2 | 5/2004 | Richelsoph |
| 6,740,089 B2 | 5/2004 | Haider |
| 6,743,231 B1 | 6/2004 | Gray |
| 6,746,449 B2 | 6/2004 | Jones et al. |
| 6,746,454 B2 | 6/2004 | Winterbottom et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,719 B2 | 7/2004 | Justis et al. |
| 6,761,723 B2 | 7/2004 | Buttermann et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,835,205 B2 | 12/2004 | Atkinson et al. |
| 6,837,889 B2 | 1/2005 | Shluzas |
| 6,840,940 B2 | 1/2005 | Ralph et al. |
| 6,843,791 B2 | 1/2005 | Serhan |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,160,300 B2 | 1/2007 | Jackson |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,250,052 B2 | 7/2007 | Landry et al. |
| 7,264,621 B2 | 9/2007 | Coates et al. |
| 7,270,665 B2 | 9/2007 | Morrison et al. |
| 7,282,064 B2 | 10/2007 | Chin |
| 7,290,347 B2 | 11/2007 | Augostino |
| 7,291,151 B2 | 11/2007 | Alvarez |
| 7,291,153 B2 | 11/2007 | Glascott |
| 7,294,128 B2 | 11/2007 | Alleyne et al. |
| 7,294,129 B2 | 11/2007 | Hawkins et al. |
| 7,306,603 B2 | 12/2007 | Boehm et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,377,922 B2 | 5/2008 | Barker |
| 7,470,279 B2 | 12/2008 | Jackson |
| 7,476,228 B2 | 1/2009 | Abdou |
| 7,476,238 B2 | 1/2009 | Panjabi |
| 7,491,208 B2 | 2/2009 | Pond, Jr. et al. |
| 7,503,918 B2 | 3/2009 | Baccelli et al. |
| 7,527,638 B2 | 5/2009 | Anderson et al. |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,588,589 B2 | 9/2009 | Falahee |
| 7,601,166 B2 | 10/2009 | Biedermann et al. |
| 7,604,653 B2 | 10/2009 | Kitchen |
| 7,604,654 B2 | 10/2009 | Fallin et al. |
| 7,611,518 B2 | 11/2009 | Walder et al. |
| 7,615,068 B2 | 11/2009 | Timm et al. |
| 7,618,443 B2 | 11/2009 | Abdou |
| 7,621,912 B2 | 11/2009 | Harms et al. |

(56) References Cited

U.S. PATENT DOCUMENTS

| | | | |
|---|---|---|---|
| 7,621,918 B2 * | 11/2009 | Jackson | 606/86 A |
| 7,621,940 B2 | 11/2009 | Harms et al. | |
| 7,625,393 B2 | 12/2009 | Fallin et al. | |
| 7,632,292 B2 | 12/2009 | Sengupta et al. | |
| 7,641,673 B2 | 1/2010 | LeCouedic et al. | |
| 7,651,502 B2 * | 1/2010 | Jackson | 606/99 |
| 7,651,515 B2 | 1/2010 | Mack et al. | |
| 7,655,026 B2 | 2/2010 | Justis et al. | |
| 7,658,739 B2 | 2/2010 | Shluzas | |
| 7,658,752 B2 | 2/2010 | Labrom et al. | |
| 7,666,188 B2 | 2/2010 | Anderson | |
| 7,682,375 B2 | 3/2010 | Ritland | |
| 7,695,475 B2 | 4/2010 | Justis et al. | |
| 7,695,496 B2 | 4/2010 | Labrom et al. | |
| 7,695,498 B2 | 4/2010 | Ritland | |
| 7,695,514 B2 | 4/2010 | Kwak | |
| 7,727,260 B2 | 6/2010 | Albert et al. | |
| 7,887,539 B2 | 2/2011 | Dunbar, Jr. et al. | |
| 2001/0001119 A1 | 5/2001 | Lombardo | |
| 2001/0007941 A1 | 7/2001 | Steiner et al. | |
| 2001/0010000 A1 | 7/2001 | Gertzbein | |
| 2001/0012937 A1 | 8/2001 | Schaffler et al. | |
| 2001/0023350 A1 | 9/2001 | Choi | |
| 2001/0025553 A1 | 10/2001 | Oesterle et al. | |
| 2001/0027318 A1 | 10/2001 | Oribe et al. | |
| 2001/0029375 A1 | 10/2001 | Betz | |
| 2001/0037111 A1 | 11/2001 | Dixon et al. | |
| 2001/0041894 A1 | 11/2001 | Campbell et al. | |
| 2001/0047173 A1 | 11/2001 | Schlapfer et al. | |
| 2001/0047174 A1 | 11/2001 | Donno et al. | |
| 2001/0047175 A1 | 11/2001 | Doubler et al. | |
| 2002/0004683 A1 | 1/2002 | Michelson | |
| 2002/0007184 A1 | 1/2002 | Ogilvie et al. | |
| 2002/0010467 A1 | 1/2002 | Cooper et al. | |
| 2002/0013586 A1 | 1/2002 | Justis et al. | |
| 2002/0016594 A1 | 2/2002 | Schlapfer et al. | |
| 2002/0022764 A1 | 2/2002 | Smith et al. | |
| 2002/0022842 A1 | 2/2002 | Horvath et al. | |
| 2002/0029040 A1 | 3/2002 | Morrison et al. | |
| 2002/0035365 A1 | 3/2002 | Kumar et al. | |
| 2002/0035366 A1 | 3/2002 | Walder et al. | |
| 2002/0035367 A1 | 3/2002 | Ritland | |
| 2002/0045898 A1 | 4/2002 | Freid et al. | |
| 2002/0045899 A1 | 4/2002 | Errico et al. | |
| 2002/0045904 A1 | 4/2002 | Fuss et al. | |
| 2002/0049446 A1 | 4/2002 | Harkey, III et al. | |
| 2002/0055740 A1 | 5/2002 | Lieberman | |
| 2002/0055741 A1 | 5/2002 | Schlapfer et al. | |
| 2002/0058942 A1 | 5/2002 | Biedermann et al. | |
| 2002/0058950 A1 | 5/2002 | Winterbottom et al. | |
| 2002/0068941 A1 | 6/2002 | Hanson et al. | |
| 2002/0068975 A1 | 6/2002 | Teitelbaum et al. | |
| 2002/0072751 A1 | 6/2002 | Jackson | |
| 2002/0077701 A1 | 6/2002 | Kuslich | |
| 2002/0082602 A1 | 6/2002 | Biedermann et al. | |
| 2002/0082603 A1 | 6/2002 | Dixon et al. | |
| 2002/0087159 A1 | 7/2002 | Thomas et al. | |
| 2002/0087161 A1 | 7/2002 | Randall et al. | |
| 2002/0091386 A1 | 7/2002 | Martin et al. | |
| 2002/0091390 A1 | 7/2002 | Michelson | |
| 2002/0095153 A1 | 7/2002 | Jones et al. | |
| 2002/0103487 A1 | 8/2002 | Errico et al. | |
| 2002/0111626 A1 | 8/2002 | Ralph et al. | |
| 2002/0111628 A1 | 8/2002 | Ralph et al. | |
| 2002/0116001 A1 | 8/2002 | Schafer et al. | |
| 2002/0120270 A1 | 8/2002 | Trieu et al. | |
| 2002/0123752 A1 | 9/2002 | Schultheiss et al. | |
| 2002/0133154 A1 | 9/2002 | Saint Martin | |
| 2002/0133158 A1 | 9/2002 | Saint Martin | |
| 2002/0133159 A1 | 9/2002 | Jackson | |
| 2002/0138076 A1 | 9/2002 | Biedermann et al. | |
| 2002/0138077 A1 | 9/2002 | Ferree | |
| 2002/0143330 A1 | 10/2002 | Shluzas | |
| 2002/0143332 A1 | 10/2002 | Lin et al. | |
| 2002/0143338 A1 | 10/2002 | Orbay et al. | |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173789 A1 | 11/2002 | Howland |
| 2002/0173791 A1 | 11/2002 | Howland |
| 2002/0193795 A1 | 12/2002 | Gertzbein et al. |
| 2002/0198526 A1 | 12/2002 | Shaolian et al. |
| 2003/0004519 A1 | 1/2003 | Torode et al. |
| 2003/0023240 A1 | 1/2003 | Amrein et al. |
| 2003/0023243 A1 | 1/2003 | Biedermann et al. |
| 2003/0055426 A1 | 3/2003 | Carbone et al. |
| 2003/0060826 A1 | 3/2003 | Foley et al. |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0149432 A1 | 8/2003 | Frigg et al. |
| 2003/0150897 A1 | 8/2003 | Ng |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176862 A1 | 9/2003 | Taylor et al. |
| 2003/0176863 A1 | 9/2003 | Ueyama et al. |
| 2003/0181913 A1 | 9/2003 | Lieberman |
| 2003/0191469 A1 | 10/2003 | Ralph et al. |
| 2003/0191470 A1 | 10/2003 | Ritland |
| 2003/0199872 A1 | 10/2003 | Markworth et al. |
| 2003/0199873 A1 | 10/2003 | Richelsoph |
| 2003/0199874 A1 | 10/2003 | Michelson |
| 2003/0208203 A1 | 11/2003 | Lim et al. |
| 2003/0208204 A1 | 11/2003 | Bailey et al. |
| 2003/0208275 A1 | 11/2003 | Michelson |
| 2003/0212398 A1 | 11/2003 | Jackson |
| 2003/0216735 A1 | 11/2003 | Altarac et al. |
| 2003/0216748 A1 | 11/2003 | Gitis et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas |
| 2004/0002708 A1 | 1/2004 | Ritland |
| 2004/0006342 A1 | 1/2004 | Altarac et al. |
| 2004/0034351 A1 | 2/2004 | Sherman et al. |
| 2004/0039384 A1 | 2/2004 | Boehm et al. |
| 2004/0039385 A1 | 2/2004 | Mazda et al. |
| 2004/0044335 A1 | 3/2004 | Kazuaki et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |

(56) References Cited

U.S. PATENT DOCUMENTS

| | | |
|---|---|---|
| 2004/0111091 A1 | 6/2004 | Ogilvie et al. |
| 2004/0116929 A1 | 6/2004 | Barker et al. |
| 2004/0122442 A1 | 6/2004 | Lewis |
| 2004/0133207 A1 | 7/2004 | Abdou |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0172022 A1 | 9/2004 | Landry et al. |
| 2004/0172025 A1 | 9/2004 | Drewry et al. |
| 2004/0172031 A1 | 9/2004 | Rubecamp et al. |
| 2004/0176766 A1 | 9/2004 | Shluzas |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0210216 A1 | 10/2004 | Farris et al. |
| 2004/0215190 A1 | 10/2004 | Nguyen et al. |
| 2004/0215191 A1 | 10/2004 | Kitchen |
| 2004/0220567 A1 | 11/2004 | Eisermann |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249378 A1 | 12/2004 | Saint Martin et al. |
| 2004/0249380 A1 | 12/2004 | Glascott |
| 2004/0254574 A1 | 12/2004 | Morrison et al. |
| 2004/0267260 A1 | 12/2004 | Mack et al. |
| 2004/0267264 A1 | 12/2004 | Konieczynski et al. |
| 2005/0010219 A1 | 1/2005 | Dalton |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0137593 A1 | 6/2005 | Gray et al. |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149053 A1 | 7/2005 | Varieur |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171542 A1 | 8/2005 | Biedermann et al. |
| 2005/0171543 A1 | 8/2005 | Timm et al. |
| 2005/0177154 A1 | 8/2005 | Moumene et al. |
| 2005/0177157 A1 | 8/2005 | Jahng |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192580 A1 | 9/2005 | Dalton |
| 2005/0192589 A1 | 9/2005 | Raymond |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228385 A1 | 10/2005 | Lee et al. |
| 2005/0228400 A1 | 10/2005 | Chao et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Cassagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0267577 A1 | 12/2005 | Trieu |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |

(56) References Cited

U.S. PATENT DOCUMENTS

| | | |
|---|---|---|
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036255 A1 | 2/2006 | Pond |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084977 A1 | 4/2006 | Lieberman |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0106394 A1 | 5/2006 | Colleran |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jojnes et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0149251 A1 | 7/2006 | Ziolo et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Falilin et al. |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195098 A1 | 8/2006 | Schumacher |
| 2006/0200023 A1 | 9/2006 | Melkent et al. |
| 2006/0200128 A1 | 9/2006 | Mueller |
| 2006/0200130 A1 | 9/2006 | Hawkins |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2006/0217716 A1 | 9/2006 | Baker et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247658 A1 | 11/2006 | Pond, Jr. et al. |
| 2006/0247779 A1 | 11/2006 | Gordon |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |

(56) References Cited

U.S. PATENT DOCUMENTS

| | | |
|---|---|---|
| 2006/0264940 A1 | 11/2006 | Hartmannt |
| 2006/0264942 A1 | 11/2006 | Lim et al. |
| 2006/0264962 A1 | 11/2006 | Chin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2006/0293693 A1 | 12/2006 | Farr et al. |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016194 A1 | 1/2007 | Shaolian et al. |
| 2007/0016198 A1 | 1/2007 | Boehm, Jr. et al. |
| 2007/0016199 A1 | 1/2007 | Boehm, Jr. et al. |
| 2007/0021750 A1 | 1/2007 | Shluzas et al. |
| 2007/0032123 A1 | 2/2007 | Timm et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073290 A1 | 3/2007 | Boehm, Jr. |
| 2007/0073291 A1 | 3/2007 | Cordaro et al. |
| 2007/0073293 A1 | 3/2007 | Martz |
| 2007/0073294 A1 | 3/2007 | Chin et al. |
| 2007/0073405 A1 | 3/2007 | Verhulst et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093827 A1 | 4/2007 | Warnick |
| 2007/0093828 A1 | 4/2007 | Abdou |
| 2007/0093831 A1 | 4/2007 | Abdelgany et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0156142 A1 | 7/2007 | Rezach et al. |
| 2007/0156237 A1 | 7/2007 | Kwak |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0233155 A1 | 10/2007 | Lovell |
| 2007/0244481 A1 | 10/2007 | Timm |
| 2007/0250061 A1 | 10/2007 | Chin et al. |
| 2007/0260246 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0270869 A1 | 11/2007 | Young et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0009862 A1 | 1/2008 | Hoffman |

(56) References Cited

U.S. PATENT DOCUMENTS

| | | |
|---|---|---|
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Norin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0114403 A1 | 5/2008 | Kuester et al. |
| 2008/0119849 A1 | 5/2008 | Beardsley et al. |
| 2008/0119857 A1 | 5/2008 | Potash et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154279 A1 | 6/2008 | Schumacher et al. |
| 2008/0154307 A1 | 6/2008 | Colleran et al. |
| 2008/0161854 A1 | 7/2008 | Bae et al. |
| 2008/0161857 A1 | 7/2008 | Hestad et al. |
| 2008/0161859 A1 | 7/2008 | Nilsson |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeronk et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228184 A1 | 9/2008 | Hestad |
| 2008/0228227 A1 | 9/2008 | Brown et al. |
| 2008/0228229 A1 | 9/2008 | Walder et al. |
| 2008/0234691 A1 | 9/2008 | Schwab |
| 2008/0234734 A1 | 9/2008 | Walder et al. |
| 2008/0234736 A1 | 9/2008 | Trieu et al. |
| 2008/0234737 A1 | 9/2008 | Bosehert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234746 A1 | 9/2008 | Jahng et al. |
| 2008/0234756 A1 | 9/2008 | Sutcliffe et al. |
| 2008/0234759 A1 | 9/2008 | Marino |
| 2008/0243052 A1 | 10/2008 | Pond et al. |
| 2008/0243185 A1 | 10/2008 | Felix et al. |
| 2008/0243188 A1 | 10/2008 | Walder |
| 2008/0243194 A1 | 10/2008 | Lotz et al. |
| 2008/0249570 A1 | 10/2008 | Carson et al. |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262551 A1 | 10/2008 | Rice et al. |
| 2008/0262552 A1 | 10/2008 | Kim |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0300630 A1 | 12/2008 | Bohnema et al. |
| 2008/0300633 A1 | 12/2008 | Jackson |
| 2008/0306513 A1 | 12/2008 | Winslow et al. |
| 2008/0306525 A1 | 12/2008 | Winslow et al. |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312655 A1 | 12/2008 | Kirschman et al. |
| 2008/0312692 A1 | 12/2008 | Brennan et al. |
| 2008/0312694 A1 | 12/2008 | Peterman et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0005817 A1 | 1/2009 | Friedrich et al. |
| 2009/0012567 A1 | 1/2009 | Biedermann et al. |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030464 A1 | 1/2009 | Hestad et al. |
| 2009/0030465 A1 | 1/2009 | Altarac et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0054932 A1 | 2/2009 | Butler et al. |

(56) References Cited

U.S. PATENT DOCUMENTS

| | | |
|---|---|---|
| 2009/0062860 A1 | 3/2009 | Frasier et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082812 A1 | 3/2009 | Lewis |
| 2009/0082815 A1 | 3/2009 | Zylber et al. |
| 2009/0088782 A1 | 4/2009 | Moumene et al. |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099599 A1 | 4/2009 | Biedermann et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0105769 A1 | 4/2009 | Rock et al. |
| 2009/0105771 A1 | 4/2009 | Lei et al. |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0118772 A1 | 5/2009 | Diederich et al. |
| 2009/0125063 A1 | 5/2009 | Panjabi |
| 2009/0131981 A1 | 5/2009 | White |
| 2009/0138052 A1 | 5/2009 | Biedermann et al. |
| 2009/0149885 A1 | 6/2009 | Durward et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0171395 A1 | 7/2009 | Jeon et al. |
| 2009/0177232 A1 | 7/2009 | Kiester |
| 2009/0192548 A1 | 7/2009 | Jeon et al. |
| 2009/0198281 A1 | 8/2009 | Rice et al. |
| 2009/0228045 A1 | 9/2009 | Hayes et al. |
| 2009/0240286 A1 | 9/2009 | Friedrich et al. |
| 2009/0240287 A1 | 9/2009 | Cunliffe et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0259257 A1 | 10/2009 | Prevost |
| 2009/0259258 A1 | 10/2009 | Perez-Cruet et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0299411 A1 | 12/2009 | Laskowitz et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2010/0010544 A1 | 1/2010 | Fallin et al. |
| 2010/0030271 A1 | 2/2010 | Winslow et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063551 A1 | 3/2010 | Richelsoph |
| 2010/0069964 A1 | 3/2010 | Lechmann |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087865 A1 | 4/2010 | Biedermann et al. |
| 2010/0094348 A1 | 4/2010 | Biedermann et al. |

FOREIGN PATENT DOCUMENTS

| | | |
|---|---|---|
| DE | 4425392 | 11/1995 |
| DE | 19507141 | 9/1996 |
| DE | 19509141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| GB | 1519139 | 7/1978 |
| GB | 9202745.8 | 4/1992 |
| GB | 2365345 | 2/2002 |
| GB | 2382304 | 5/2003 |
| JP | 10277070 | 10/1998 |
| JP | 2000325358 | 11/2000 |
| SU | 313538 | 10/1971 |
| WO | 8912431 | 12/1989 |
| WO | 9116020 | 10/1991 |
| WO | WO92/03100 | 3/1992 |
| WO | 9321848 | 11/1993 |
| WO | 9410944 | 5/1994 |
| WO | WO94/10927 | 5/1994 |
| WO | WO94/26191 | 11/1994 |
| WO | 9428824 | 12/1994 |
| WO | 9531947 | 11/1995 |
| WO | 9606576 | 3/1996 |
| WO | 9621396 | 7/1996 |
| WO | 9628105 | 9/1996 |
| WO | 9628118 | 9/1996 |
| WO | WO96/41582 | 12/1996 |
| WO | 9714368 | 4/1997 |
| WO | 9727812 | 8/1997 |
| WO | 9801091 | 1/1998 |
| WO | 9815233 | 4/1998 |
| WO | 9825534 | 6/1998 |
| WO | 9832386 | 7/1998 |
| WO | 9834554 | 8/1998 |
| WO | 9838924 | 9/1998 |

(56) References Cited

FOREIGN PATENT DOCUMENTS

| | | |
|---|---|---|
| WO | 9905980 | 2/1999 |
| WO | 9938463 | 8/1999 |
| WO | 9947083 | 9/1999 |
| WO | 0022997 | 4/2000 |
| WO | 0027297 | 5/2000 |
| WO | 0065268 | 11/2000 |
| WO | 0066045 | 11/2000 |
| WO | 0110317 | 2/2001 |
| WO | 0115612 | 3/2001 |
| WO | 0128435 | 4/2001 |
| WO | WO01/28436 | 4/2001 |
| WO | WO01/45576 | 6/2001 |
| WO | 0149191 | 7/2001 |
| WO | 0167972 | 9/2001 |
| WO | 0167974 | 9/2001 |
| WO | 0234150 | 5/2002 |
| WO | WO02/054966 | 7/2002 |
| WO | WO02/102259 | 12/2002 |
| WO | 03007828 | 1/2003 |
| WO | WO03/026523 | 4/2003 |
| WO | 03047442 | 6/2003 |
| WO | WO03/068088 | 8/2003 |
| WO | 2004022108 | 3/2004 |
| WO | WO2004/041100 | 5/2004 |
| WO | WO2004/075778 | 9/2004 |
| WO | WO2004/089245 | 10/2004 |
| WO | 2004098452 | 11/2004 |
| WO | WO2004/107997 | 12/2004 |
| WO | WO2005/000136 | 1/2005 |
| WO | WO2005/000137 | 1/2005 |
| WO | 2005018466 | 3/2005 |
| WO | WO2005/020829 | 3/2005 |
| WO | 2005030068 | 4/2005 |
| WO | WO2005/065374 | 7/2005 |
| WO | WO2005/065375 | 7/2005 |
| WO | WO2005/072632 | 8/2005 |
| WO | 2005087121 | 9/2005 |
| WO | WO2005/082262 | 9/2005 |
| WO | WO2005/099400 | 10/2005 |
| WO | 2005102195 | 11/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | WO2006/028537 | 3/2006 |
| WO | 2006042188 | 4/2006 |
| WO | WO2006/045094 | 4/2006 |
| WO | 2006047711 | 5/2006 |
| WO | 2006066685 | 6/2006 |
| WO | 2006079531 | 8/2006 |
| WO | WO2006/086537 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO 2007/124249 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | 2009015100 | 1/2009 |
| WO | WO2005/013839 | 2/2009 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

Brochure of Tyco/Healthcare/Surgical Dynamics on Spiral Radius 90D, Publication Date: Sep. 2001, pp. 1-8.
Brochure of Zimmer Spine, Inc., Dynesys® LIS Less Invasive Surgery, The Dynamic Stabilization System, Publication Date: 2005.
CD Horizon M8 Multi Axial Screw Spinal System Brochure, Medtronic Sofamor Danek, no publish date.
Claris Instrumentation Brochure, G Med, pub. 1997.
Contour Spinal System Brochure, Ortho Development, no publish date.
EBI Omega 21 Brochure, EBI Spine Systems, pub. 1999.
SDRS Surgical Dynamics Rod System Brochure, Surgical Dynamics, pub. 1998-99.
The Rod Plate System Brochure, Stryker Howmedica Osteonics, pub. Oct. 1999.
Versalok Low Back Fixation System Brochure, Wright Medical Technology, Inc., pub. 1997.
VLS System Variable Locking Screw Brochure, Interpore Cross International, 1999.
Brochure of Spinal Concepts, *Pathfinder, Minimally Invasive Pedicle Fixation System*, Publication Date: May 2003.
Brochure of Spinal Concepts, an Abbott Laboratories Company, *Pathfinder, Minimally Invasive Pedicle Fixation System*, Publication Date: Nov. 2003.
Brochure of Spinal Concepts, Surgical Technique, *InCompass, Thoracolumbar Fixation System*, Publication Date: Oct. 2003.
Brochure of SpineLine, Current Concepts, *Minimally Invasive Posterior Spinal Decompression and Fusion Procedures*, Publication Date: Sep./Oct. 2003.
Brochure of Sofamor Danek the Spine Specialist, TSRH, *Pedicle Screw Spinal System*, Publication Date: Jan. 23, 1995.
Brochure of DePuySpine on Surgical Technique, Published 2004, pp. 1-36.

* cited by examiner

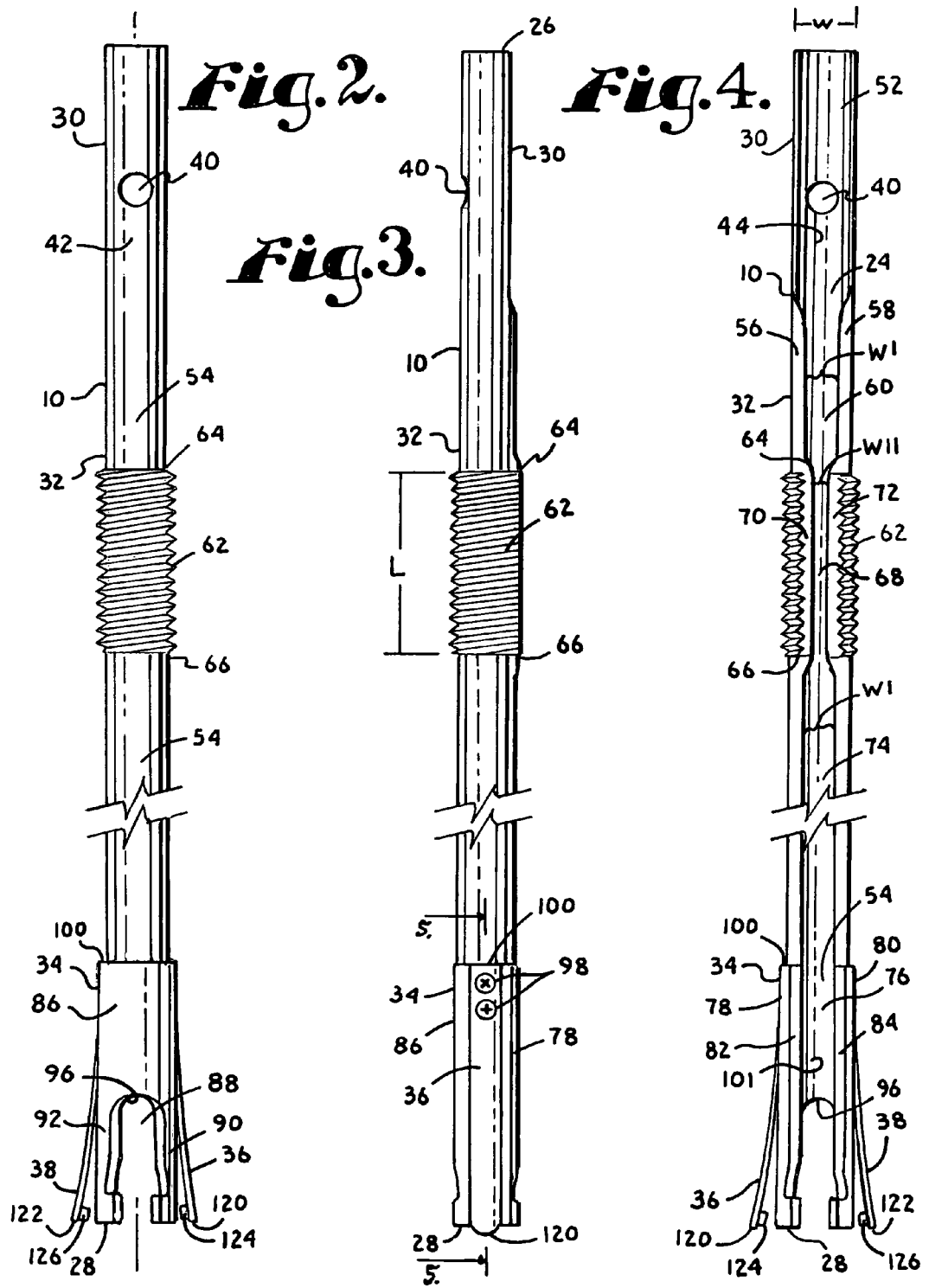

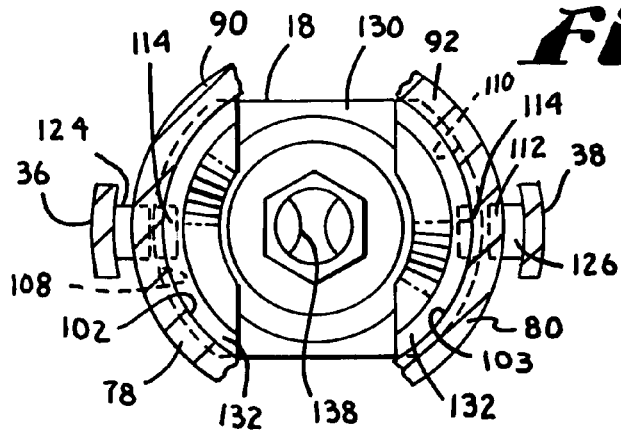
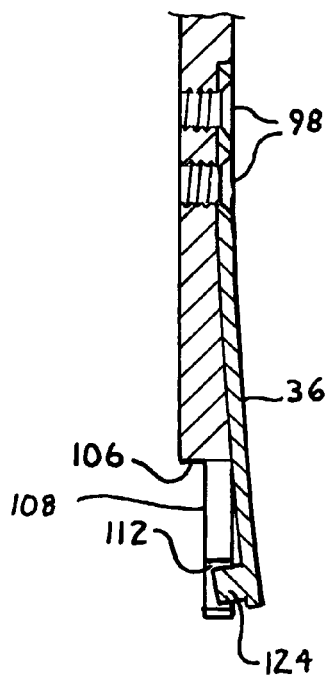
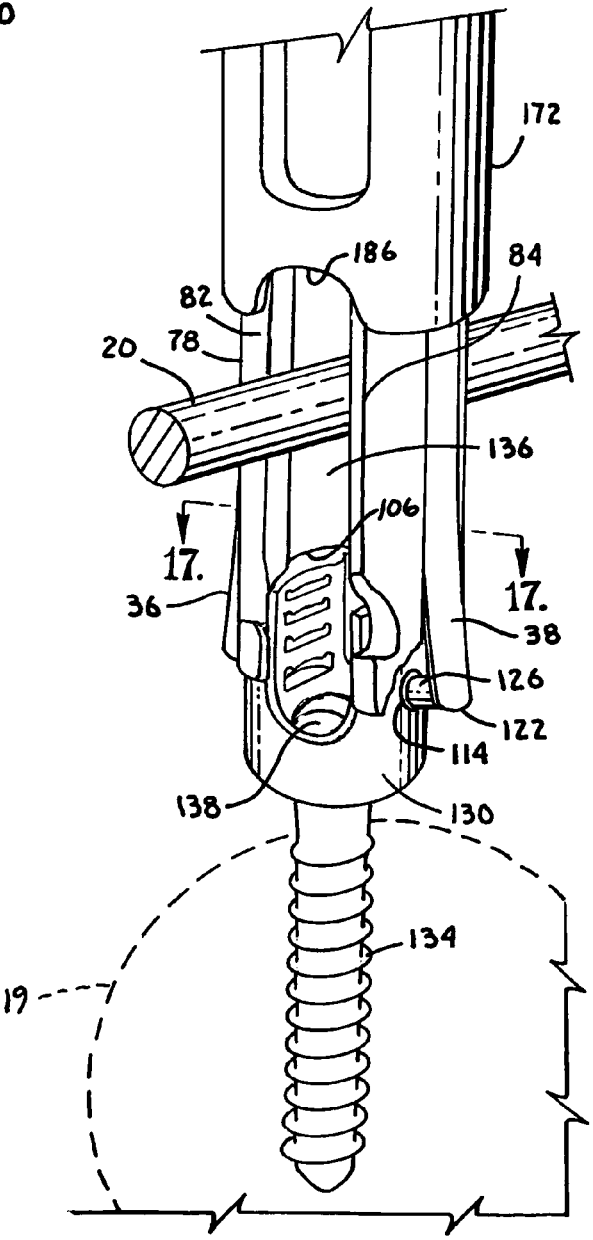

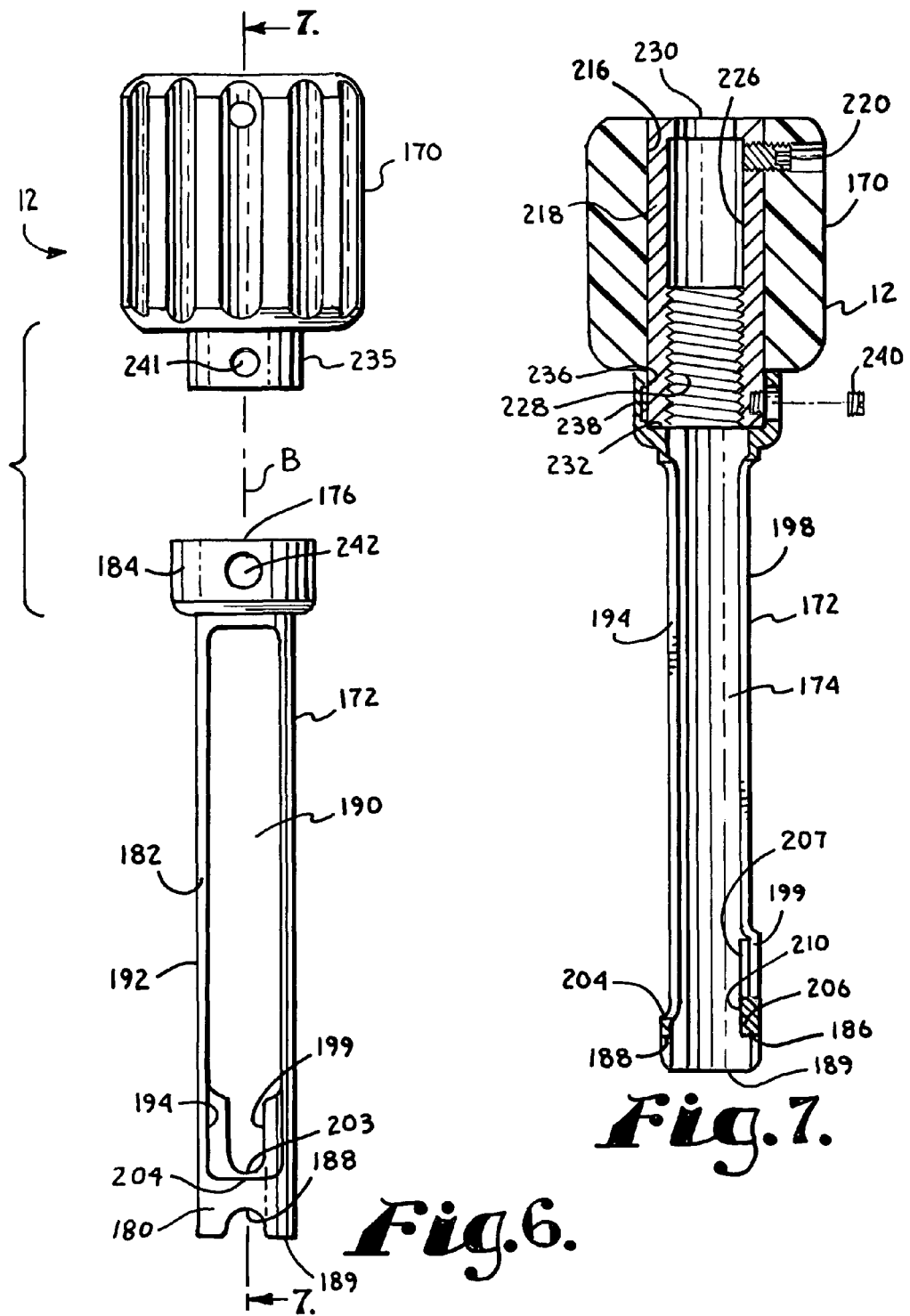

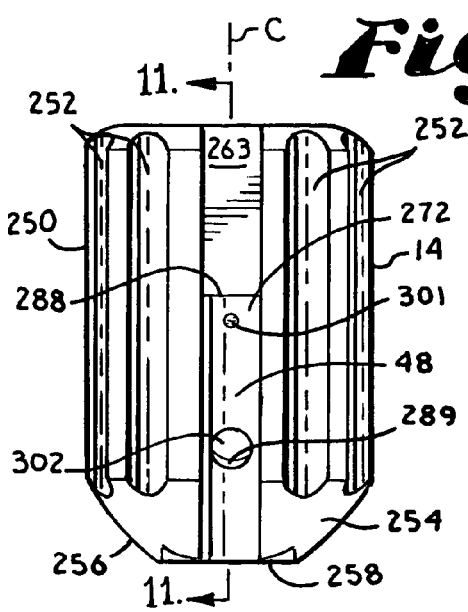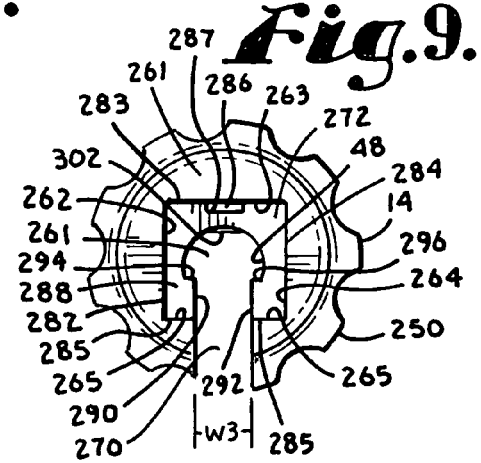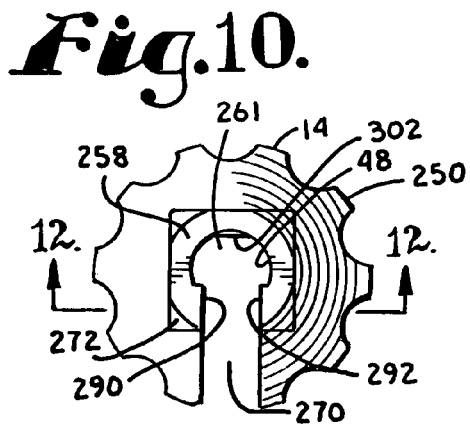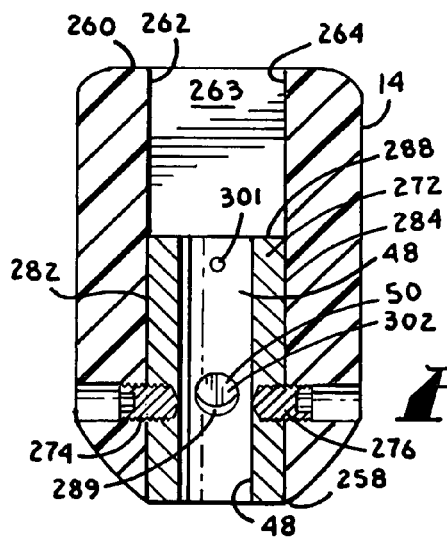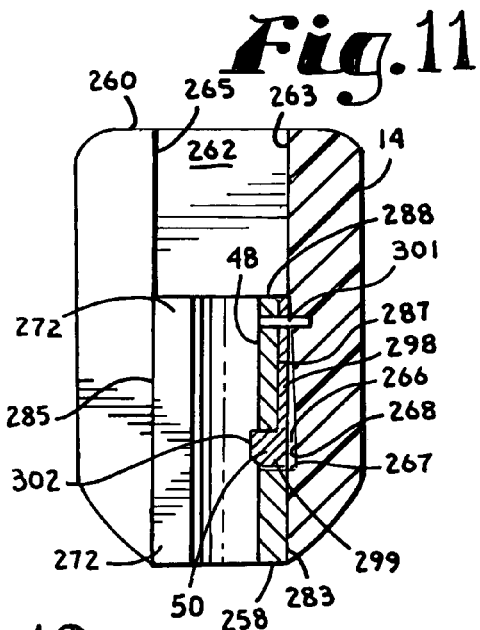

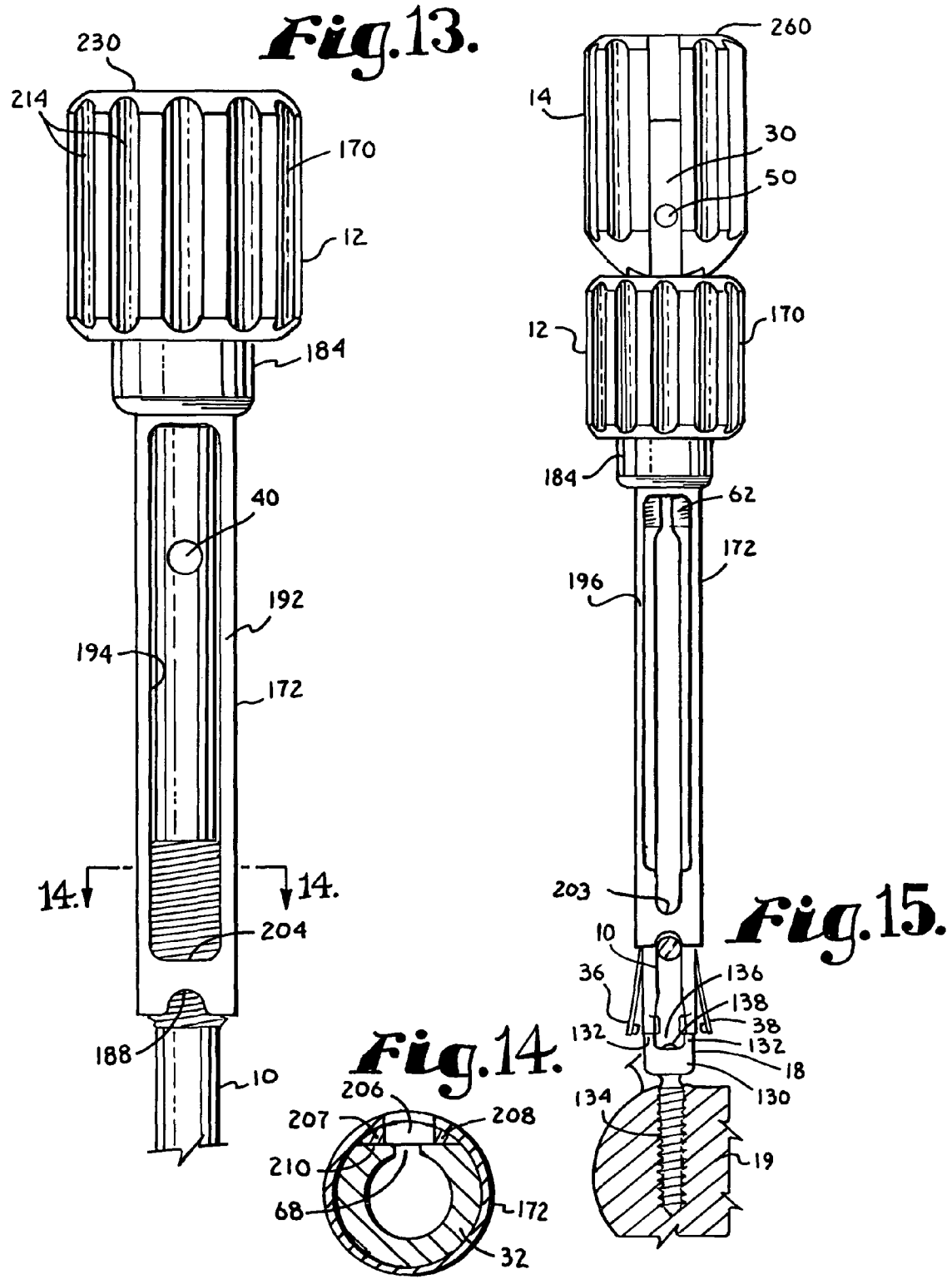

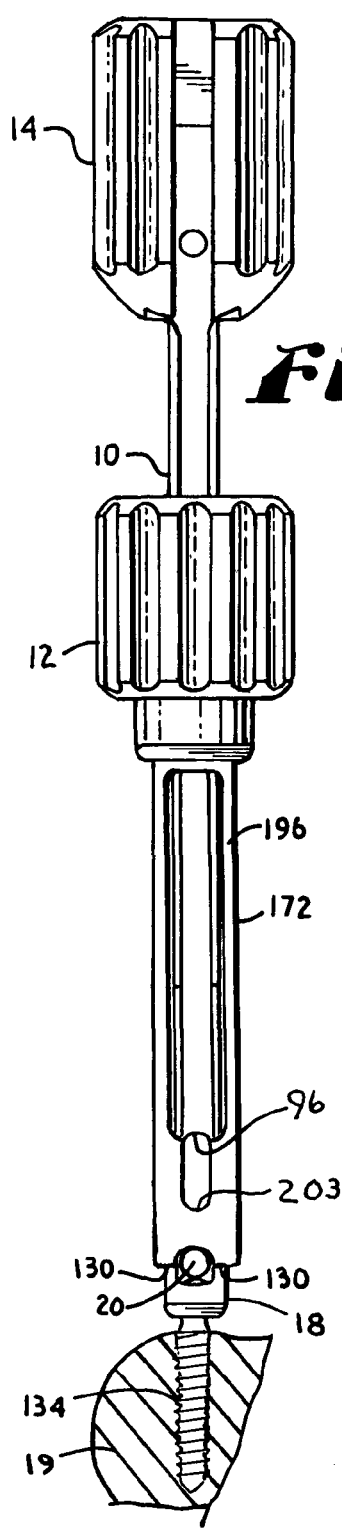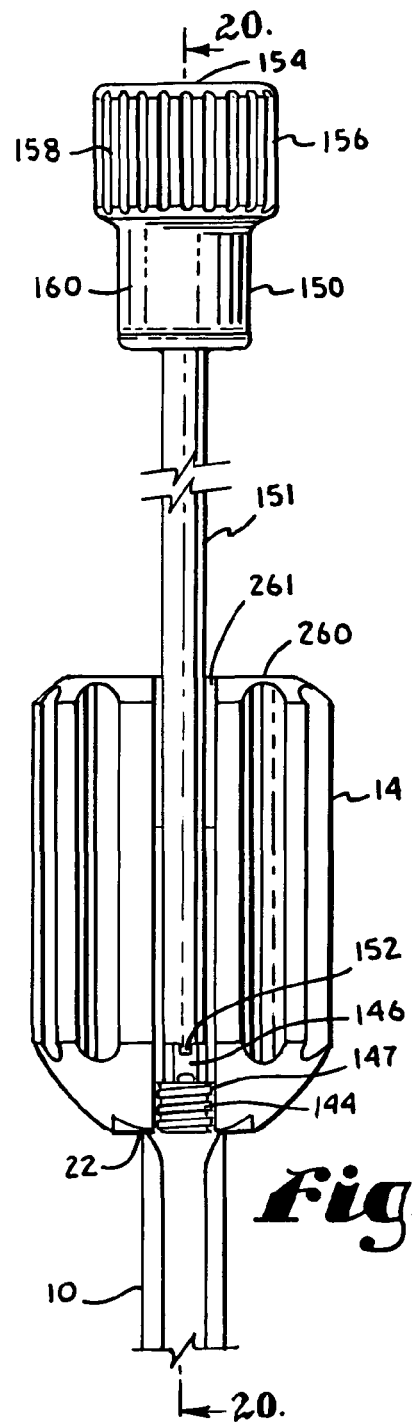

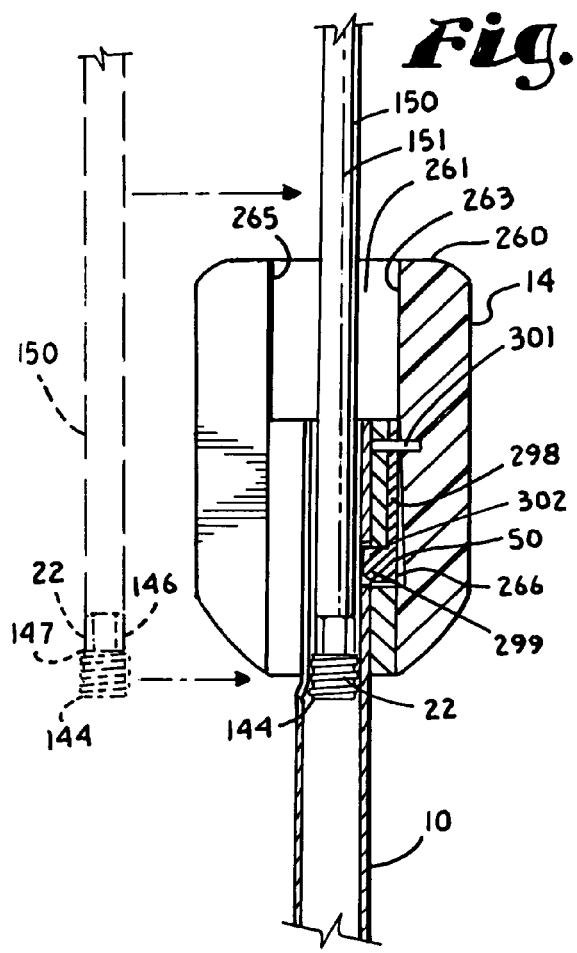
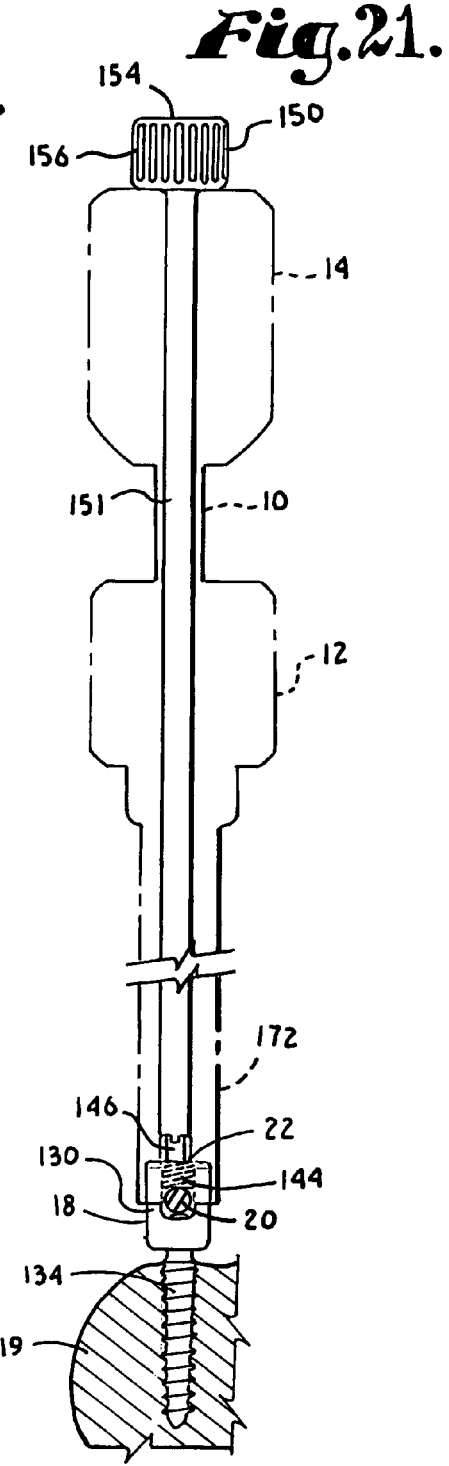

SPINAL FIXATION TOOL SET AND METHOD FOR ROD REDUCTION AND FASTENER INSERTION

CROSS REFERENCE TO RELATED APPLICATIONS

This application is a continuation of U.S. patent application Ser. No. 10/950,377, filed Sep. 24, 2004 now U.S. Pat. No. 7,651,502, which is incorporated by reference herein.

BACKGROUND OF THE INVENTION

The present invention relates to apparatuses and methods for use in performing spinal surgery and, in particular, to tools and methods of using such tools, especially for implanting a rod for spinal support and alignment.

For many years, spinal osteosynthesis apparatuses have been utilized to correct spinal deformities, injuries or disease. In such procedures, elongate rods are surgically attached to vertebrae of the spine to provide support and/or to realign or reposition certain vertebrae. Such rods are secured to vertebrae utilizing bone screws and other spinal implants. In particular, bone screws with open ended heads are often utilized for such surgery, with the rod being placed into an open end of one or more implants and then the open end or ends being closed or capped to secure the rod to the implant.

Rods utilized in spinal surgery are often bent or formed to support the spine in a desired manner, or to exert a desired corrective or stabilizing force on the spine. Thus, to obtain such a desired alignment, rods must often be forced into open ended spinal implants.

In order to reduce the impact of such surgery on the patient, a desirable approach is to utilize implanting tools and procedures that have a low profile, resulting in less trauma to the body of the patient. Problems arise when implantation tools designed for traditional surgery that is highly invasive are utilized. The tools may be bulky, oversized or have irregular surfaces or protrusions. A projecting actuator arm or fastening member may provide adequate mechanical advantage to force a rod into a head of an implant, but there may be insufficient clearance to use such structure and/or such structure may produce additional trauma or damage to the patient.

Consequently, it is desirable to develop apparatuses and techniques that allow for the securing of a rod to a bone screw or other implant already attached to a vertebra with significantly less invasion into the body of the patient. At the same time, it is desirable to develop such apparatuses and techniques that provide adequate mechanical advantage to force the rod into position within the bone screw and thereafter hold the rod in place during closing or capping of the bone screw head.

SUMMARY OF THE INVENTION

A guide tool structure or assembly according to the invention is provided for implanting a spinal rod into bone screws or other spinal implants already implanted in a bone. The tool includes an elongate guide structure having a handle structure at one end thereof and opposed implant engaging structure at another end thereof. The implant engaging end is configured for releaseable attachment to an implanted bone screw or other spinal implant. The guide member body defines a channel having a lateral opening along an entire length thereof. The channel is sized and shaped for side loading and receiving of an implant fastener or closure member at one or more loading locations intermittently positioned along the length of the channel. Preferably, side loading is performed at the handle structure.

An embodiment of a tool assembly according to the invention further includes an elongate installation tool or rod pushing member having a translation nut and an attached sleeve. The translation nut is coaxial with the sleeve and freely rotatable with respect thereto. The nut is configured for rotatable attachment to the guide member. In a particular embodiment according to the invention, the guide member has an outer surface with a first guide and advancement structure thereon, such as a helically wound thread, and the translation nut has an inner surface having a second guide and advancement structure thereon, mateable with the first guide and advancement structure. Thus, rotation of the translation nut when the first and second guide and advancement structures are mated causes non-rotating axial translation of the sleeve along the guide member.

In an embodiment according to the invention, the sleeve includes a rod pushing end that functions both to press or reduce a rod into a spinal implant and also to radially press against the guide member end into engagement with the spinal implant.

The assembly may further include a handle, preferably configured for releaseable attachment to the guide member. In particular, in an embodiment according to the invention, the handle has a spring-loaded pin configured to project into an aperture disposed on an upper portion of the guide member when the handle is received on the guide member. The handle includes a channel configured for coaxial alignment with the guide member channel, and a lateral opening configured for coaxial alignment with the guide member lateral opening. The handle lateral opening is configured for receiving a manipulation tool and other spinal implant components, such as a closure top or other spinal implant members utilized for attaching a rod to the spinal implant.

In a particular embodiment according to the invention, a guide member includes a bone screw attachment end having first and second legs defining first and second lateral openings for receiving a rod therethrough. Furthermore, the first leg defines a first slot and the second leg defines a second slot. First and second opposed spring tabs are attached to the first and second legs, respectively. Each spring tab has a protrusion or projection configured for projecting through one of the slots, and into an aperture of a bone screw or other spinal implant. The first and second spring tabs bias the protrusions away from the first and second slots. When assembled with the installation tool or rod pushing member, the spring tabs are pressed radially inwardly by an inner surface of the rod pushing member, which in turn urges the guide member protrusions into bone screw or other spinal implant apertures.

Thus, the assembly according to the invention may be described as having two different configurations. In a first implant receiving configuration, the installation tool is received on the guide member, the nut rotatably attached to the guide member, the handle received on the guide member with the spring-loaded pin disposed in the aperture and the handle in contact with the translation nut. In such configuration, the spring tabs are biased radially outwardly to an extent that the protrusions or projections are not projecting completely through the slots defined by the legs.

In a second, spinal implant holding and rod reducing position, the translation nut is spaced from the handle, and the sleeve of the installation tool is pressing against the spring tabs, urging the protrusions or projections into and through the slots of the guide tool, and if properly aligned with a spinal implant, projecting the protrusions into the spinal implant apertures, thus attaching the guide member to the implanted bone screw or spinal implant.

The rod pushing member sleeve may then be translated downwardly toward the implant, by rotating the translation nut, the rod pushing end pressing a rod downwardly into the implant and holding the rod within the implant during attachment of a closure top or other closure structure onto the spinal implant utilizing the laterally opening channel in the handle for the insertion of closure structure components down the guide member channel and onto the spinal implant. Furthermore, after a rod is attached to the spinal implant, the guide member and attached rod pushing member are easily and readily removed from the implant by simple translation of the rod pushing member sleeve up and off outer surfaces of the spring tabs.

OBJECTS AND ADVANTAGES OF THE INVENTION

Therefore, the objects of the present invention are: to provide a low profile, compact tool assembly for supporting bone screws and installing other implants with minimal trauma to the patient; to provide a tool assembly for implanting a spinal rod for support or alignment along a human spine with minimal trauma to the patient; to provide such a tool assembly including a guide member for slidably guiding a rod toward a bone screw attached to the guide member; to provide such a tool assembly including rod and implant fastener installation tools for assisting in securing the rod in the bone screws; to provide such a tool assembly wherein the guide member is easily and readily attached to and disengaged from bone screws; to provide such a tool assembly wherein the guide member, rod reduction tool, and closure top installation tools are all easily aligned, positioned, and engaged, if necessary, with respect to the bone screw and are disengaged from the bone screw and other tools in the installation assembly by manual manipulation of the surgeon; to provide a method of implanting a rod into bone screws within a patient with minimal surgical trauma to the patient; and to provide such a tool assembly and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is a partial rear elevational view of the guide member of FIG. 1.

FIG. 3 is a partial side elevational view of the guide member of FIG. 2.

FIG. 4 is a partial front elevational view of the guide member of FIG. 2.

FIG. 5 is a cross-sectional view, taken along the line 5-5 of FIG. 2.

FIG. 6 is an exploded rear elevational view of the rod pushing member of FIG. 1.

FIG. 7 is a cross-sectional view of the rod pushing member, taken along the line 7-7 of FIG. 6.

FIG. 8 is the front elevational view of the handle shown in FIG. 1.

FIG. 9 is a top plan view of the handle of FIG. 8.

FIG. 10 is a bottom plan view of the handle of FIG. 8.

FIG. 11 is a cross-sectional view of the handle taken along the line 11-11 of FIG. 8.

FIG. 12 is a cross-sectional view of the handle taken along the line 12-12 of FIG. 10.

FIG. 13 is a partial rear elevational view of the guide member and rod pushing member of FIG. 1 shown at an early stage of installation.

FIG. 14 is a cross-sectional view, taken along the line 14-14 of FIG. 13.

FIG. 15 is a reduced front elevational view of an assembled guide member, rod pushing member and handle of FIG. 1, further shown mounted onto a bone screw implanted in a vertebra, with the rod pushing member in an implant receiving position.

FIG. 16 is an enlarged perspective view similar to FIG. 15, with portions broken away to show the detail thereof.

FIG. 17 is an enlarged cross-sectional view, taken along the line 17-17 of FIG. 16.

FIG. 18 is a reduced front elevational view of the assembled guide member, rod pushing member, handle and bone screw of FIG. 15, shown fully installed in a vertebra, with a rod.

FIG. 19 is an enlarged and partial front elevational view of the handle and assembled guide member of FIG. 17 shown with a closure top manipulation tool and a closure top.

FIG. 20 is an enlarged and partial cross-sectional view of the handle and guide member taken along the line 20-20 of FIG. 19 shown with a closure top manipulation tool and a closure top and further illustrating a side-loading procedure for inserting the closure top manipulation tool and closure top into the handle and guide member assembly (shown in phantom).

FIG. 21 is a reduced and partially schematic view of the assembly of FIG. 18, shown with a closure top installed on the bone screw, the bone screw implanted in a vertebra.

DETAILED DESCRIPTION OF THE INVENTION

Figure 1:
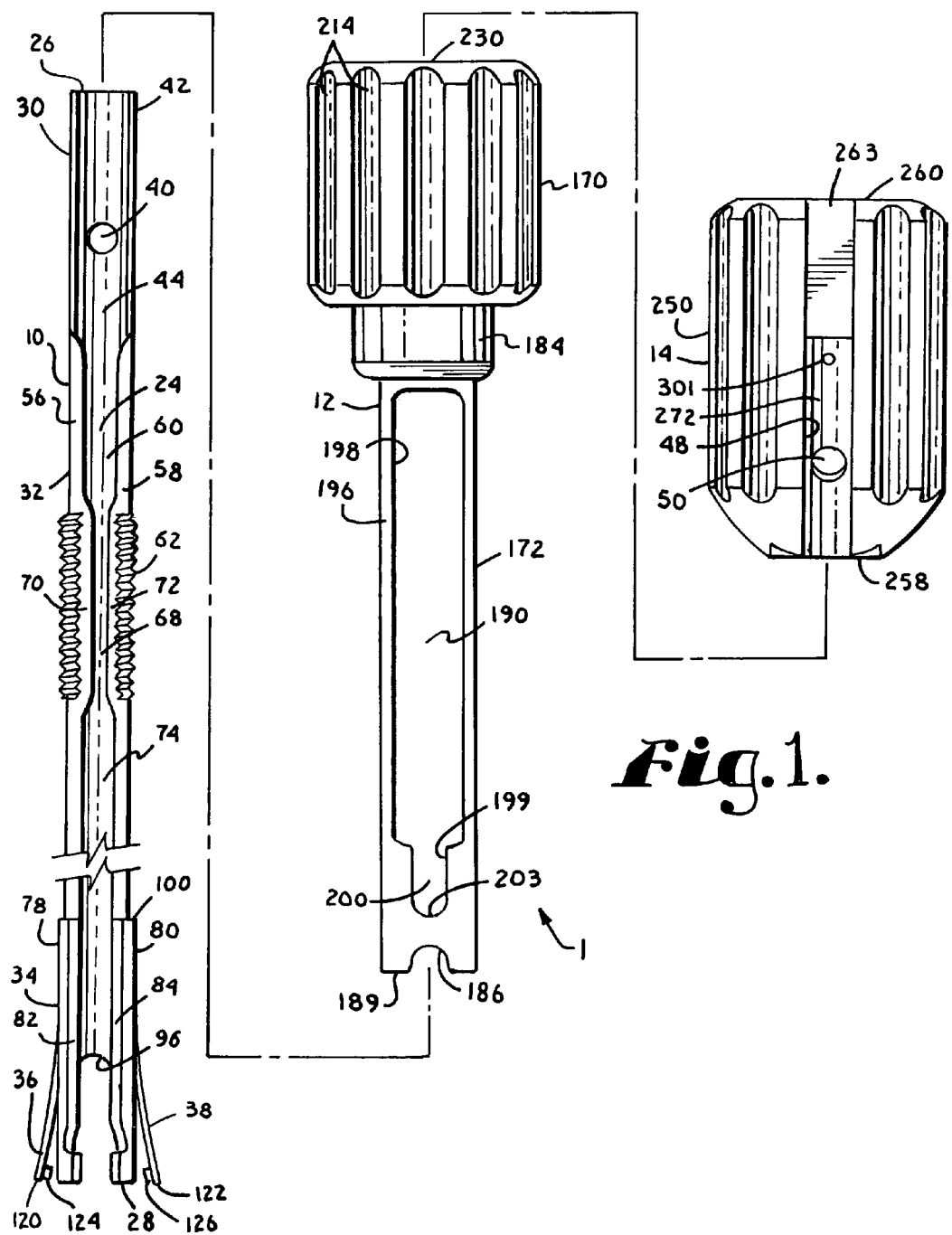
FIG. 1 is an exploded and partial front elevational view of a tool assembly according to the present invention showing an elongate guide member, a rod pushing member, and a handle.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

With reference to FIG. 1, reference numeral 1 generally designates a tool assembly according to the present invention, including a guide structure or member 10 configured for releaseable attachment to a bone screw, attachable to a rod pushing member 12 configured to function as an installation tool that not only pushes or reduces a rod into a bone screw but also presses the guide member into contact and attachment with the bone screw. Also attachable to the guide member 10 is a handle or holder 14 configured to also function as a side-loading manipulation tool guide and support.

The assembly 1 is configured for use with a spinal implant, such as a bone screw 18 that has previously been implanted in a vertebra 19 and a rod 20, also previously inserted in the vicinity of the bone screw 18. The assembly 1 is utilized for reducing the rod 20 or other elongate member into a head of the bone screw 18, and for installing a fastener, such as a closure top 22 or other closure structure to the bone screw 18, capturing the rod 20 within the bone screw 18. The assembly 1 is a particularly helpful tool when the rod 20 is bent relative to the location of the vertebra 19 (which is sometimes the case) to which the rod 20 is to attach and is not easily placed in a head of the bone screw 18 without force. The assembly 1 provides mechanical advantage in such situations. Although not shown, a plurality of assemblies 1 according to the invention may be used as a set for spinal implant procedures so that one guide member 10 is used for each implanted bone screw 18 to which a rod 20 is to be attached. Rods 20 or other longitudinal members are often installed on both sides of the spine during the same procedure.

The elongate guide member 10 is best illustrated in FIGS. 1-5. The elongate guide member 10 is somewhat cylindrical in outer profile. With respect to inner profile, the guide member 10 forms a channel 24 with elongate lateral openings of various widths, configured to receive, contain and allow translational movement along the channel 24, or rotational relative movement of certain tools, as described more fully below. The channel 24 extends from a top 26 to a bottom 28 of the member 10, parallel to a central axis of rotation A thereof. The channel 24 is sized to accommodate elongate tools and bone screw components, such as the fastener or closure structure 22. The guide member 10 is sized and shaped to be sufficiently long to extend from an implanted bone screw 18 through an exterior of a patient's skin, so as to provide an outwardly extending upper or handle portion 30 for attachment to the handle 14, and also for gripping by a surgeon during procedures utilizing the guide member 10, with or without an attached installation tool or rod pushing member 12 and/or handle 14. The guide member 10 further includes an intermediate portion 32 equipped for attachment to the rod pushing member or installation tool 12, and a lower bone screw or other implant engaging portion 34 having opposed implant engaging members, such as the opposed, flexible, implant engaging spring tabs or prongs 36 and 38, for securing a bone screw 18 or other implant there between. It is noted that any reference to the words top, bottom, upper and lower, and the like, in this application refers to the alignment shown in the various drawing figures, as well as the normal connotations applied to such devices, and is not intended to restrict positioning of the assembly 1 in actual use.

The guide member 10 upper or handle portion 30 is substantially in the form of a half-cylinder, having a C- or U-shape, end- or cross-section as viewed from the top 26. Disposed centrally in the handle portion 30 is a round aperture 40 that extends from an outer surface or back wall 42 to an inner surface or inner wall 44. The handle portion 30 cooperates with a C-shaped surface formation 48 of the handle 14, illustrated in FIGS. 8 and 9 and discussed more fully hereafter. The aperture 40 is configured and positioned to cooperate with a spring-attachment mechanism 50 disposed on the handle 14, also described more fully hereafter. At the handle portion 30, the inner wall 44 defines the channel 24 and has an elongate, substantially uniform opening 52, opening at the top 26 and having a side-to-side width W, slightly smaller than, or approximately equal to, a diameter of the handle portion 30.

At the intermediate portion 32, a curved, substantially semi-cylindrical back wall 54 is integral to and extends from the handle portion 30. The intermediate portion 32 also includes curved side walls 56 and 58, integral to the back wall 54, the side walls 56 and 58 forming an elongate, substantially uniform channel opening 60 with a side-to-side width W' that is smaller than the width W of the opening 52 at the handle portion 30. The width W of the upper portion 30 is sized and shaped to receive tools and implants, such as the closure structure 22, while the width W' of the intermediate portion 32 is narrower than a width or diameter of the closure structure 22, allowing for the retention of the closure structure 22 within the guide member 10.

Centrally located on the intermediate portion 32 is an outer, helically wound, discontinuous, guide and advancement structure 62 disposed on outer surfaces of the curved back wall 54 and both of the curved side walls 56 and 58. The guide and advancement structure 62 illustrated in the drawing figures is a conventional helically wound V-type thread. However, it is foreseen that buttress threads, helically wound square threads, or other guide and advancement structures may be utilized to cooperate with equivalent or mateable structure within the rod pushing member 12, described more fully below.

The guide and advancement structure 62 extends from an upper location 64 to a lower location 66. Between the upper location 64 and the lower location 66, a channel opening 68 communicating with the channel opening 60, narrows to a substantially uniform side-to-side width W". Thus, the channel 24 has the most narrow width W" along a length L of the guide and advancement structure 62. To form the narrow width W", the side walls 56 and 58 extend to include integral wall extensions 70 and 72, respectively, also along the length L. The wall extensions 70 and 72 are substantially co-planar and have a smooth, flat surface. The flat wall extensions 70 and 72 aid in providing a guide for orienting and installing the rod pushing member 12 with respect to the guide member 10 as will be described more fully below. Between the guide and advancement structure 62 and the lower portion 34, the walls 56 and 58 form a channel opening 74 that has the same side-to-side width W' as the channel opening 60.

The lower implant engaging portion 34 has a channel opening 76 with the same side-to-side width W' as the channel openings 60 and 74. All of the channel openings, 52, 60, 68, 74 and 76 communicate to provide a lateral opening disposed along an entire length of the guide member 10. The channel opening 76 is sized and shaped to slidingly receive a rod 20 therein. It is foreseen that the channel opening 68 may include width variations to allow for side loading of a fastener into the channel 24.

Also at the lower portion 26, the substantially cylindrical side walls 56 and 58 extend to the bottom 28 of the guide member 10 and further include integral, outer side walls 78 and 80, respectively. The walls 78 and 80 uniformly increase the thickness of the respective side walls 56 and 58. The walls 78 and 80 are configured with co-planar, flat and smooth front surfaces or facets 82 and 84, respectively, that are also coplanar with the wall extensions 70 and 72, providing for alignment and mating with an interior of the rod pushing member 12 to ensure that the guide member 10 is retained in a selected, non-rotatable position with respect to the rod pushing member 12 when installed therein.

The cylindrical back wall 54 also extends into the lower portion 34 of the guide member 10. Integral thereto is a curved back wall support 86 having a radially extending thickness approximately equal to the radial thickness of the walls 78 and 80, similarly uniformly increasing the thickness of the back wall 54. Formed in the back wall support 86 is a slot or channel opening 88, disposed between and defined by first and second back legs, 90 and 92. The slot 88 is disposed opposite the channel opening 76, and an upper portion thereof has a substantially uniform side-to-side width equal to the width W' of the channel opening 76, for receiving a rod 20 therethrough. An upper, curved rod abutment arch or surface 96, defines an upper end of the slot 88, the arch 96 for contacting the rod 20 as the guide member 10 is inserted on the bone screw 18 as will be described more fully subsequently herein. It is foreseen that the back wall 54 and the back wall support 86 may include a narrow slot or slit extending upwardly axially from the arch 96 for providing increased flexibility when inserting the guide member 10 on a bone screw 18 or other implant. Such a slit would render the outwardly biasing spring tabs 36 and 38 unnecessary, allowing for opposed implant engaging members on the guide member 10 to spring apart and thus be snapped or twisted on and off a bone screw or other implant. It is also foreseen that in other embodiments according to the invention, the location of the arch 96 may be moved axially upward, to near the intermediate portion 32 of the guide member 10, providing an elongate through-slot to allow for use of the assembly 1, for example, in a percutaneous procedure wherein the rod 20 is laterally inserted and received in such slot after the member 10 is attached to the bone screw 18.

Disposed between the back wall support 86 and the walls 78 and 80 are the spring tabs 36 and 38, respectively. The tabs 36 and 38 are elongate and fixed to the lower portion 34 with screws 98 disposed near a ledge 100 formed by substantially flush upper end surfaces of the walls 78 and 80, the back wall support 86, and the spring tabs 36 and 38. With the exception of the facets 82 and 84, near the ledge 100, the side walls 78 and 80, the back wall support 86, and the spring tabs 36 and 38 cooperate to form a substantially cylindrical outer surface having an outer diameter greater than an outer diameter of the intermediate portion 32.

Also near the ledge 100, the side walls 56 and 58 and the back wall 54 form an integral, curved, inner surface 101, sized and shaped to accept a closure structure 22 therethrough, but sized smaller than a width or diameter of a head of a bone screw 18. At the rod abutment arch 96, the inner surface 101 divides into two inner surfaces or legs 102 and 103, separated by the slot 88. Near the bottom 28 of the guide member 10, the inner surfaces 102 and 103 are recessed, with a discontinuous bone screw abutment surface or stop 106 partially defining the recess. The abutment surface 106 is substantially annular and disposed perpendicular to the axis A. Inner surfaces 108 and 110 disposed adjacent and substantially perpendicular to the abutment surface 106 also define the recess and are configured to extend about arms of a head of a bone screw 18, substantially following the curvature thereof, slidingly mating therewith along the axis A. Furthermore, the inner surfaces 108 and 110 are configured to align a rod receiving channel in the bone screw 18 with the channel opening 76 and the slot 88 and prohibiting rotational movement of the bone screw 18 about the axis A when the screw 18 abuts the surface 106. Located at the bottom 28 and extending centrally through each of the surfaces 108 and 110 are u-shaped apertures or slots 112 configured to expose apertures 114 in the bone screw 18 to the spring tabs 36 and 38 when the guide member 10 is disposed about the bone screw 18 with the bone screw 18 abutting the abutment surface 106. The slots 112 are disposed in diametrically opposed relation when viewed in cross-section.

With reference to FIG. 3, both of the spring tabs 36 and 38 extend from the ledge 100 to distal ends 120 and 122 that are disposed slightly below the bottom 28 of the guide member 10. Disposed on an inner surface of each spring tab 36 and 38, near respective distal ends 120 and 122, are diametrically opposed implant engaging protrusions or pins 124 and 126, respectively. The tabs 36 and 38 bias outwardly away from the axis A, such that, when the guide member 10 is not installed in the rod pushing member 12, the tabs 36 and 38 splay radially outwardly from the guide member 10 with the protrusions 124 and 126 disposed outside of a periphery of the side walls 78 and 80. However, compression of the tabs 36 and 38 toward the axis A causes the protrusions 124 and 126 to be received in the slots 112. As will be discussed more fully below, when the guide member 10 is slidably received on a bone screw 18, and the rod pushing member or installation tool 12 is mounted on the guide member 10, the protrusions 124 and 126 align with apertures 114 on the bone screw 18 and extend through the slots 112 and into the apertures 114, fixing the bone screw 18 to the guide member 10 when the rod pushing member 12 substantially contacts and compresses the spring tabs 36 and 38. It is noted that other orientations and sizes of protrusions 124 and 126, or other opposed implant engaging structure may be utilized according to the invention, with such structure cooperating with respective features on the guide member 10 and bone screw 18. It is further foreseen that the guide member 10 may be configured for receiving the bone screw 18 from a side thereof, for example, the slot 88 may be of increased width to allow for lateral insertion of the guide member 10 onto the bone screw 18.

The guide member 10 cooperates and mates with a head 130 of the bone screw 18 at upper arms 132 thereof. The apertures 114 identified above are rounded diametrically opposed formations, centrally located in each of the arms 132. With reference to FIGS. 14, 15 and 19, each of the bone screws 18 further includes a threaded shank 134 attached to the head 130, the shank 134 for screwing into and seating in a vertebra 19 that is part of the human spine. The arms 132 of the head 130 define a rod receiving channel 136 passing therethrough. The bone screw shank 134 includes an upper portion 138 that extends into the head 130 and is operationally secured therein, so that the head 130 is rotatable on the shank 134 until locked in position through engagement with the rod 20 under pressure. For example, the shank 134 may be connected to the head utilizing a spline capture connection as disclosed in U.S. Pat. No. 6,716,214 from Ser. No. 10/464, 633, which is incorporated by reference herein.

The closure structure, top or fastener 22 closes between the spaced bone screw arms 132 to secure the rod 20 in the channel 136. The closure top 22 can be any of many different plug type closures. With reference to FIGS. 19-20, preferably the closure top 22 has a cylindrical body with a helically wound mating guide and advancement structure 144. The guide and advancement structure 144 can be of any type, including V-type threads, buttress threads, reverse angle threads, or square threads. Preferably the guide and advancement structure 144 is a helically wound flange form that interlocks with a reciprocal flange form as part of a guide and advancement structure on an interior of the bone screw arms 132. A suitable locking guide and advancement structure of this type is disclosed in U.S. Pat. No. 6,726,689 from Ser. No. 10/236,123 which is incorporated herein by reference.

Each closure structure 22 also preferably includes a break-off head 146 that breaks from the threaded cylindrical body 144 in a break-off region 147 upon the application of a preselected torque, such as 95 to 120 inch-pounds. The break-off head 146 preferably has a hexagonal cross section faceted exterior that is configured to mate with a similarly shaped socket of a final closure driving or torquing tool (not shown).

Also preferably, the break-off head 145 has an inner cylindrical surface and a pass-through slot configured to cooperate with an elongate manipulation tool 150. The tool 150 has an elongate body 151 configured and sized for insertion into the guide member 10 and handle 14, with a break-off head engaging end that includes a projection receivable into the inner cylindrical surface of the break-off head 145 and a pair of diametrically opposed pins 152 receivable in the head 145 pass through slot. The break-off engaging end may include a slot or other feature to provide for sufficient frictional engagement between the tool 150 and the closure structure 22 so that the closure structure 22 does not slip off the tool 150 as the structure 22 is placed into the handle 14 and the guide member 10 as will be described more fully below. It is foreseen that different configurations of manipulation tool engaging ends may be utilized, depending upon the geometry of the closure structure 22.

At an opposite end or top 154, the manipulation tool 150 has a handle 156 that is substantially cylindrical in shape and is shown with an end portion having outer grooves 158 to aid a surgeon in axially handling and controlling the tool 150 and rotating the closure structure 22. The handle 156 further includes a lower portion 160 that is also substantially cylindrical, but smooth and having a smaller diameter than a diameter of the end grooved portion 158. The lower portion 160 is integral to or otherwise attached to both the end grooved portion 158 and the elongate body 151.

The present invention is not intended to be restricted to a particular type of bone screw or bone screw closure mechanism. In the present embodiment, a polyaxial type bone screw 18 is utilized wherein the shank 134 is locked in position by direct contact with the rod 20. It is foreseen that the tool assembly 1 of the present invention can be used with virtually any type of bone screw, including fixed monoaxial and polyaxial bone screws of many different types wherein the head is locked relative to the shank by structure other than in the manner described in the illustrated embodiment.

With reference to FIGS. 1 and 6-7, the installation tool or rod pushing member 12 of the tool assembly 1 of the invention preferably includes an upper translation nut 170 rotatably and free wheelingably attached to a lower guide member retaining and rod pushing sleeve 172. The sleeve 172 has an inner substantially cylindrical surface 174 defining a substantially hollow passageway 176 sized and shaped to slidingly receive the guide member 10 therein. Alternatively, is foreseen that the sleeve could have an inner and outer planar surface. The sleeve 172 is elongate and includes a receiving end portion 180, a substantially cylindrical outer body 182 and a translation nut attachment end portion 184 disposed opposite the receiving end portion 180. Near the receiving end portion 180, the sleeve inner surface 174 is configured for contacting the spring tabs 36 and 38 of the guide member 10 and pressing the tabs 36, 38 through the slots 112 and into the apertures 114 of a bone screw 18.

The receiving end portion 180 not only functions to receive the guide member 10 into the sleeve 172, but also includes a pair of diametrically opposed U-shaped arches 186 and 188, both adjacent a bottom 189 of the sleeve 172. The arches 186 and 188 are sized and configured for curving about a rod 20, and for pressing the rod downwardly into a bone screw 18 while restricting any lateral movement of the rod 20 during translation of the rod 20 toward the bone screw head 130 by rotation of the translation nut 170, when the rod pushing member 12 is installed on the guide member 10, as will be discussed more fully below.

The sleeve 172 further defines an elongate squared-off through-slot or opening 190. With reference to FIG. 6, at a rear side 192 of the sleeve 172, the slot 190 is defined by a substantially rectangular border or perimeter 194. The rear side 192 also defines the arch 188. With reference to FIG. 1, at a front side 196, the pass-through slot 190 is defined in part by a substantially rectangular border or perimeter 198 that is diametrically opposed and a mirror image of the border 194, with the exception of a lower substantially U-shaped border 199, defining a U-shaped opening or slot 200. The substantially U-shaped border 199 on the front side 196 does not have a similar or mirror-image component on the rear side 192. The slot 200 defined by the U-shaped border 199 has a side-to-side width approximately equal to the width W' of the channel openings 60, 74 and 76 of the guide member 10. The U-shaped slot 200 is centrally located on the front side 196 of the sleeve 172 and is defined in part by a base portion 203 that is spaced from the arch 186. The base portion 203 is substantially diametrically opposed to a base 204 of the substantially rectangular border 194, the base 204 spaced from the arch 188 a distance slightly less than a distance separating the base portion 203 from the arch 186.

With reference to FIG. 14, the inner surface 174 of the cylindrical portion 202, has a plate 206 fixed thereto disposed between the base 203 of the U-shaped slot 200 and the arch 186. The plate 206 also includes plate extensions 207 and 208, extending upwardly on either side of the slot 200. The plate 206 and extensions 207 and 208 are coplanar, forming a smooth, flat inner surface 210 substantially parallel to an axis B of the rod pushing member 12. The plate 206 and extensions 207 and 208 are integral or otherwise fixed, such as by welding, to the inner cylindrical surface 174. The planar surface 210 provides structure for installing the guide member 10 in a mating and desired alignment with respect to the rod pushing member 12 with the surface 210 slidably contacting the co-planar surfaces 70 and 72 during insertion of the guide member 10 into the rod pushing member 12. Thereafter, the co-planar facets 82 and 84 contact the surface 210, with the surface 210 preventing axial rotation of the member 10 with respect to the sleeve 172, resulting in a preferred alignment of the arches 186 and 188 with the lower channel opening 74 and the slot 88. The plate 206 extends to the arch 186, providing added thickness, and thus mechanical advantage where the arch 186 contacts with a rod 20 when the rod pushing member 12 pushes the rod 20 toward a bone screw 18.

The translation nut 170 of the rod pushing member 12 is substantially cylindrical in shape and is shown with outer grooves 214 to aid a surgeon in handling the rod pusher 12 and rotating the nut 170. With reference to FIG. 7, the nut 170 further includes an inner cylindrical surface 216 for fixed attachment to a substantially cylindrical insert 218 utilizing screws or pins 220. The cylindrical insert 218 also defines an inner substantially cylindrical passage 226 communicating with the passage 176 of the sleeve 172. The inner surface 216 further includes a helical guide and advancement structure as shown by a V-shaped thread 228 that is configured to mate with the guide and advancement structure 62 of the guide member 10.

Also with reference to FIG. 7, the inner cylindrical surface 216 extends from an upper open end 230 of the translation nut 170 to an inner annular seating surface 232 of the sleeve 172, the surface 232 extending radially outwardly and perpendicular to the cylindrical surface 216. The guide and advancement structure 228 terminates at the seating surface 232. As will be discussed more fully below, the surface 216 with associated thread 228 is of a length that provides an equivalent translation distance of the rod pushing member 12 with respect to the guide member 10 such that the arches 186 and 188 can be used to gradually push the rod 20 toward the bone screw 18 for the entire translation distance by rotating the nut 170 until the rod 20 is fully seated in the head of the bone screw. It is foreseen that other structure may be utilized to provide for translation of the sleeve 172 along the guide member 10, such as a frictional or ratchet structure.

Further with reference to FIG. 7, at the annular seating surface 232, the sleeve 172 is in sliding, rotational contact with the nut 170 about the axis B. The insert 218 includes a lower portion 235 extending below the translation nut 170 and disposed opposite the upper open end 230. The translation nut attachment portion 184 of the sleeve 172 defines an inner cylindrical surface 236 of slightly greater diameter than an outer diameter of the insert portion 235. The surface 236 is configured to slidingly receive the nut lower portion 235 along the surface 236. The sleeve 172 further defines an annular recess or groove 238 configured to receive a screw 240 rigidly fixed to the insert lower portion 235 at an aperture 241. The screw 240 may be accessed for attachment and removal from the lower portion 235 through an aperture 242 disposed in the sleeve translation nut attachment portion 184. The screw 240 slidingly mates with the sleeve portion 184 that defines the recess 238, keeping the nut 170 and sleeve 172 in an attached, but freely rotatable relation.

With reference to FIGS. 8-12, the handle 14 of an assembly 1 according to the invention is preferably detachable and includes an outer, substantially cylindrical surface 250 shown with grooves 252 to aid a surgeon in handling the assembly 1 for assembly of the handle 14 with the guide member 10, insertion of the guide member 10 on a bone screw 18 and for stationary gripping and stability during rotation of the rod pusher translation nut 170. The cylindrical surface 250 is disposed substantially parallel to an axis C of the handle 14. At a lower portion 254 of the handle 14, an outer, substantially conical surface 256 extends from the cylindrical surface 250 toward the axis C, to a substantially flat lower end or bottom surface 258, disposed perpendicular to the axis C. The handle 14 also includes a substantially flat top surface 260 parallel to the bottom surface 258.

The handle 14 further defines an elongate through-bore 261 extending centrally along the axis C from the top surface 260 to the bottom surface 258, the bore 261 being defined in part by substantially planar, rectangular, inner surfaces 262, 263, 264 and 265. With the exception of a portion of the surface 263, each of the surfaces 262, 263, 264 and 265 are disposed substantially parallel to the axis C and form substantially square end- and cross-sections as illustrated in FIGS. 9 and 10. However, the surface 263 also forms a recess 266 defined by a flat, rectangular surface portion 267 disposed substantially perpendicular to the axis C and a flat, rectangular surface portion 268 disposed at an angle slightly less than 90 degrees with respect to the surface portion 267, the surface portion 268 extending between the surface portion 267 and a portion of the surface 263 disposed substantially parallel to the axis C. The recess 266 receives the spring attachment 50 as discussed more fully below.

The surface 265 is discontinuous, broken by an elongate slot 270 formed in the handle 14, extending from the top surface 260 to the bottom surface 258, the slot 270 communicating with the bore 261 along an entire length thereof. The slot 270 opens laterally to the surface 250 and has a side-to-side width W3 that is larger than the width W'. The width W3 is also slightly larger than a diameter of the threaded cylindrical body 144 of the closure structure 22. The slot 270 is configured to laterally receive the manipulation tool 150 and an attached closure structure 22 or other fastener, and allow radial movement thereof toward the axis C until the tool 150 is disposed centrally in the bore 261. Thereafter, the bore 261 accommodates translational movement therealong and rotational movement of the tool 150, as described more fully below. It is foreseen that according to the invention, the rod pushing member 12, at both the nut 170 and sleeve 172, may also include a slot with a lateral opening of a width and orientation to operably communicate with the slot 270 of the handle 14 and the channel 24 of the guide member 10.

An insert 272 is disposed within the bore 261 and fixedly attached to the handle 14 at the planar inner surface 262 by a pin 274 and at the planar inner surface 264 by a pin 276. Outer, substantially planar and rectangular surfaces 282, 283, 284 and 285 are contiguous to and contact the inner surfaces 262, 263, 264 and 265 respectively, with the pin 274 extending through the surface 282 and the pin 276 extending through the surface 284. Similar to the surface 265, the surface 285 is discontinuous and broken by the elongate slot 270. The surface 283 includes an upper elongate recess 286 disposed centrally therein and defined in part by a planar surface 287 disposed spaced from and parallel to the surface 283. The recess 286 communicates fully with the slanted recess 266 formed in the inner surface 263. The surface 287 originates at a top planar surface 288 of the insert 272 and terminates at a rounded aperture 289 formed in the insert 272. The aperture 289 is spaced from the bottom 258 of the handle 14 and extends radially from the surface 283 and the surface 287 to the C-shaped inner surface 48. The recess 286 and the aperture 289 are configured for receiving the spring attachment 50, described more fully below.

The insert 272 extends from the bottom surface 258 to the top planar surface 288. The top planar surface 288 is disposed within the bore 261, spaced from the top 260, and is oriented substantially parallel to the top 260 and perpendicular to the axis C. The C-shaped surface 48 partially defines an inner portion of the insert 272 and partially defines the through-bore 261. Parallel walls 290 and 292 partially define the slot 270 and co-planar connecting walls 294 and 296 are disposed between the C-shaped surface 48 and respective walls 290 and 292. The co-planar walls 294 and 296 provide abutment surfaces for the alignment and attachment of the upper portion 30 of the guide member 10 with respect to the handle 14.

The spring attachment 50 is substantially L-shaped in cross-section as shown in FIG. 11, having an upper leg 298 and a lower leg or protrusion 299 integral and substantially perpendicular to the upper leg 298. The upper leg 298 is fixed between the handle inner surface 263 and the insert surface 287 by a pin 301 disposed near the insert top surface 288. The upper leg 298 has a thickness slightly less than a distance between the surface 283 and the surface 287 at the recess 286. Thus, near the insert top surface 288, the upper leg 298 preferably contacts both the insert surface 287 and the inner surface 263, with the surface 263 and the pin 301 urging the upper leg 298 in contact with the surface 287 along a length thereof. The lower leg or protrusion 299 is configured to extend through the aperture 298, having an end portion 302 extending beyond the C-shaped surface 48 and into the bore 261. The end portion 302 is configured to be received by the aperture 40 of the guide member 10. When a radial outward force is placed on the end portion 302, the protrusion 299 is urged into the aperture 298 and the upper leg 298 extends into the recess 266 formed in the handle surface 263. Such a radial force is placed on the end portion 302 when a guide member 10 is received into the bore 261 as will be described more fully below.

With reference to FIGS. 1 and 13-18, a three-component assembly 1 according to the invention including the guide member 10, rod pushing member 12 and the handle 14 is assembled as follows: The guide member 10 is inserted into the rod pushing member 12 with the upper end 26 being inserted into the receiving end or bottom 189 of the rod pushing member 12. The guide member 10 is received into the rod pushing member 12 with the channel opening 52 facing the arch 186 and the U-shaped slot 200, and the outer surface or back wall 42 facing the arch 188 and the substantially rectangular border 194 as shown in FIG. 13. As the guide member 10 is received into the rod pushing member 12, rotational movement is prevented by the flat surface 210 of the plate 206 and plate extensions 207 and 208, in sliding contact with the flat wall extensions 70 and 72 of the guide member 10. The translation nut 170 is then rotated clock-wise as viewed from the upper end 230, with the thread 62 of the guide member 10 mating with the thread 228 disposed on the inner surface of the translation nut 170. The translation nut 170 is then rotated until the entire upper or handle portion 30 of the guide member 10 is positioned outside of the upper end 230 of the nut 170, and to where the side walls 56 and 58 begin, with a small section of the thread 62 exposed by the slot 190 as shown in FIG. 15.

During rotation of the translation nut 170, the guide member 10 is held in position and any rotational movement of the member 10 is prevented by the alignment plate 206 and extensions 207 and 208 in contact with the co-planar walls or facets 82 and 84 of the guide member 10.

With reference to FIG. 15, after installation of the rod pushing member 12 to the guide member 10, the handle 14 is inserted into the guide member 10 exposed upper or handle portion 30 by inserting the portion 30 into the bore 261 at the bottom 258 of the handle 14 with the outer back wall 42 in contact with the C-shaped surface 48 and the channel opening 52 facing the slot 270. The handle portion 30 is slid axially along the C-shaped surface and into the bore 261 with the back wall 42 forcing the spring attachment end portion 302 into the aperture 289, thereby forcing the spring attachment 50 into the recess 266, until the aperture 40 of the guide member 10 is aligned with the aperture 289. Upon such alignment, the spring attachment 50 biases the end portion 302 back through the aperture 289 and also through the guide member aperture 40, fixing the handle 14 to the guide member 10. During assembly of the handle 14 onto the guide member 10, the axial and radial alignment of the aperture 40 with respect to the aperture 289 is provided by the abutment walls 294 and 296 disposed at either side of the C-shaped surface 48, contacting edges of the guide member portion 30 that define the channel opening 52, and thus prohibiting rotational movement of the handle 14 with respect to the guide member 10.

With reference to FIGS. 15-17, the axes A, B, and C of the assembly 1 are now aligned and the assembly 1 is in a bone screw or other implant engaging configuration, with the channel 24 aligned with the bore 261. In such configuration, the rod pushing member sleeve 172 is disposed about the guide member lower portion 235, but at a distance from the bottom 28 of the guide member 10 such that the sleeve 172 does not bias the spring tab protrusions 125 and 126 completely through the slots 112. However, in the implant engaging position, the sleeve 172 is preferably placing some pressure on the spring tabs or prongs 36 and 38, with the respective protrusions 124 and 126 disposed partially within the slots 112 as shown in FIG. 17 in readiness for bone screw attachment.

In use, the assembly 1 is utilized to attach one or more rods 8 to the human spinal column 6. The procedure is begun by selection of a bone screw 18 in accordance with the size of the patient's vertebra 19 and the requirements of the spinal support needed. Bone screws 18 having a rotatable or polyaxial head 130 are preferred but not required for the procedure, as such allow relatively easy adjustment of a rod 20. Preferably the assembly 1 is utilized in a traditional, open procedure, wherein a long incision is made along the spinal column to accommodate the length of the rod, the bone screws 18 are then implanted, followed by the rod 20. After placement of the rod along the length of the incision to a location near the bone screws 18, the assembly 1 is inserted over the rod 20 and onto a bone screw 18. However, it is foreseen that in certain minimally invasive or percutaneous procedures, the guide member 10 may be attached to the bone screw 18, followed by lateral insertion of the rod 20 through the slot or lateral opening 88 of the member 10.

The bone screws 18 are typically implanted into a bone, such as the vertebra 19, by rotation of the shank 134 using a suitable driving tool (not shown) that operably drives and rotates the shank 134 by engagement thereof with apertures or other tool engagement apparatus located at or near the upper portion of the shank 138. It is foreseen that before the bone screw 18 is implanted in the vertebra 19 it may be desirable to attach an elongate guide tool (not shown) to the bone screw head 130, utilizing the apertures 114. Such a guide tool (not shown) is of a length similar to the guide member 10 so as to aid a surgeon in holding and placement of the bone screw 18, and also provide stability during the bone screw driving process.

After the rod 20 is inserted near the implanted bone screw or screws 18, an assembly 1 according to the invention is preferably attached to the bone screw 18 to provide mechanical advantage for pushing the rod 20 into the bone screw head 130. The assembly 1 of the invention is typically attached to the bone screw 18 after the rod 20 is positioned in the vicinity of the bone screw head or heads 130, as close as possible to respective rod receiving channels 136. The assembly 1, configured in the implant engaging position shown in FIG. 15 is then guided downwardly through an incision (not shown) to straddle the rod 20 within the slot or channel opening 88 of the guide member 10 and between the back legs 90 and 92 and the front facets 82 and 84. The assembly 1 is then joined to a bone screw 18 by inserting the lower implant engaging portion 34 about the bone screw head 130, aligning the slot 88 with the bone screw rod receiving channel 136, with the guide member lower portion 34 and associated spring tabs 36 and 38 aligned with the upper arms 132 as shown in FIGS. 15-17. The assembly 1 is then slid along the bone screw head 130 until the head 130 contacts the abutment surface 106. Any rotational movement between the assembly 1 and the head 130 is prohibited by the inner sleeve surface 174 that is configured to follow the curvature of the head upper arms 132 and partially wrap about edges of the arms 132. The translation nut 170 is then rotated in a clock-wise direction, as viewed from the handle 14, lowering the sleeve 172 along the spring tabs 36 and 38 and biasing the tabs radially inwardly, with the protrusions 124 and 126 projecting through the U-shaped slots 112 and into the bone screw apertures 114, thereby fixing the bone screw 18 to the assembly 1. The surgeon turns the translation nut 170 with one hand while holding the assembly 1 at the handle 14 with the other hand, providing support and stability during attachment of the assembly 1 to the bone screw 18. When the rear arch 188 of the rod pushing member 12 is co-aligned and substantially flush with the rod abutment arch 96 of the guide member 10, the protrusions 124 and 126 are seated fully within the bone screw apertures 114. An advantage of the assembly 1 according to the invention is that no twisting or other rotational or lateral movement occurs during attachment of the assembly 1 to the bone screw 18 that may cause trauma to human tissue. All twisting and rotation movement is performed outside the skin at the translation nut 170.

As already mentioned herein, it is foreseen that in certain minimally invasive procedures, it may be desirable to first insert the assembly 1, or possibly just the guide member 10, onto an implanted bone screw 18 and thereafter slide the rod 20 through the slot 88, capturing the rod 20 between the bone screw head 130 and the rod abutment arch 96 and/or arches 186 and 188 of the rod pusher 12.

After the assembly 1 is attached to the bone screw 18, the rod 20 is pushed downwardly into the rod receiving channel 136 and then into abutment with the upper shank portion 138, by rotating the translation nut 170 in a clockwise direction (as viewed from above the handle 14), thereby translating the sleeve 172 in a downward direction toward the bone screw 18, with the plate 206 abutting and pushing against the rod 20. The translation nut 170 is rotated clockwise until the rod 20 is seated against the upper shank portion 138 as shown in FIG. 18.

As shown in FIG. 19-21, after the rod 20 is positioned within the bone screw 18, a fastener or closure structure 22 is transported down the channel 24 utilizing the manipulation tool 150. It is foreseen that it may also be desirable to additionally push the rod 20 toward the screw 18, simultaneously with the rod reduction performed by rotating the translation nut 170. As shown in FIGS. 19 and 20, the closure structure 22 attached to the manipulation tool 150 is placed in the elongate top to bottom channel 24 of the guide member 10, preferably by entry from the side through the slot 270 of the handle 14 that communicates fully with the channel 24 at the upper handle portion 30 of the guide member 10. The manipulation tool 150 is moved laterally through the slot 270 until both the closure structure 22 and the tool 150 are disposed centrally in the channel 24, which is also centrally located in the bore 261 of the handle 14. The manipulation tool 150 is then moved downwardly through the channel 24 toward the bone screw 18. Alternatively the closure structure 22 that has been attached to the manipulation tool 150 may be inserted into the bore 261 at the top 260 of the handle 14 and then moved down the channel 24. As the closure structure 22 and tool 150 pass through the intermediate portion 32 of the guide member 10, the side walls 56 and 58 prohibit passage of the closure structure 22 out of the channel 24 and further provide axial alignment of the elongate body 151 of the tool 150.

Once the closure structure 22 abuts against the upper arms 132 of the bone screw 18, the manipulation tool 150 is rotated in a clockwise direction, mating a helically wound guide and advancement structure disposed on inner surfaces of the bone screw arms 132 with the threaded cylindrical body 144 of the closure structure 22, so as to drive the closure structure 22 downward against the rod 20 and to further urge the rod 20 downward into the bone screw channel 136. With reference to FIG. 21, continued rotation of the tool 150, utilizing the handle 156, drives the rod 20 downward and into engagement with the upper portion of the bone screw shank 138, so as to snug against and frictionally lock the shank 134 in position relative to the bone screw head 130.

Once all of the closure structures 22 or other fasteners utilized in a particular procedure are in final seated position in respective bone screws 18 and the surgeon is satisfied with the position of all of the elements, the manipulation tool 150 is removed by pulling upwardly and sliding the tool 150 out of the assembly 1 through the channel 24. The assembly 1 is then removed from the bone screw 18 by rotating the translation nut 170 counter-clockwise until the translation nut top 230 abuts the handle bottom 258. As the sleeve 172 moves upward and off of the spring tabs 36 and 38, the protrusions 124 and 126 spring out of the apertures 114, freeing the assembly 1 from the bone screw 18. Then, the assembly 1 is pulled upwardly, out of the incision.

If desired, a torquing tool (not shown) is then inserted into the incision and utilized to engage with the break-off head 146 and apply a preselected torque, which breaks the head 146 from the closure top 22, and is thereafter removed.

It is to be understood that while certain forms of the present invention have been illustrated and described herein, it is not to be limited to the specific forms or arrangement of parts described and shown.

What is claimed and desired to be secured by Letters Patent is as follows:

1. An elongate guide tool comprising:
   a) a handle structure at a first end of a guide member;
   b) an opposed implant engaging structure at a second end of the guide member; and
   c) a channel defining surface extending from the first end to the second end and having a lateral opening that extends an entire length of the guide member, the lateral opening being sized and shaped for side loading and receiving of an implant fastener into a loading location positioned along the length of the channel.

2. The guide tool of claim 1 wherein the loading location is at the handle structure.

3. The guide tool of claim 1 further comprising a rod pushing member attachable to the guide tool.

4. The guide tool of claim 1 having an external guide and advancement structure.

5. The guide tool of claim 4 wherein the guide and advancement structure is a thread.

6. The guide tool of claim 4 wherein the guide and advancement structure is a first guide and advancement structure, and further comprising a rod pushing member having a second guide and advancement structure mateable to the first guide and advancement structure.

7. The guide tool of claim 1 wherein the implant engaging structure includes a pair of radially opposed and flexible implant engaging members, each of the implant engaging members having a radially inwardly extending protrusion.

8. The guide tool of claim 1 wherein the implant engaging structure has a pair of opposed spring tabs biasing radially outwardly from the guide tool.

9. The guide tool of claim 1 wherein the handle structure is detachable.

10. The guide tool of claim 1 wherein the lateral opening has a varying width.

11. A spinal rod implantation tool assembly comprising:
    a) an elongate guide member having an end configured for releasable attachment to a spinal implant and a first channel defining surface having a first lateral opening extending along an entire length of the guide member;
    b) an elongate installation tool having
       I) a translation nut configured for rotatable attachment to the guide member, and
       ii) an attached sleeve with a rod pushing end translatable along the guide member and operably urging the spinal implant and a rod together, the translation nut being coaxial and freely rotatable with respect to the sleeve; and
    c) a handle configured for releasable attachment to the guide member, the handle having
       I) a second channel defining surface configured for coaxial alignment with the first channel defining surface, and
       ii) a second lateral opening configured for coaxial alignment with the first lateral opening, the second lateral opening configured for receiving a manipulation tool.

12. The assembly of claim 11 further comprising:
a) a manipulation tool having a holder and a stem, the stem being laterally insertable into the handle second channel so as to be in coaxial relationship with both the first and second channels and having an end configured for rotatable engagement with a closure member of a spinal implant.

13. A guide member for use with a spinal implant bone screw with first and second side apertures and an associated rod, the guide member comprising:
a) an elongate body having an inner surface defining an elongate channel, the body further defining a first elongate lateral opening communicating with the channel and extending an entire length of the elongate body; and
b) a bone screw attachment end having
I) first and second legs defining in part the first lateral opening; and
ii) first and second opposed spring tabs, the first spring tab secured to the first leg and including a first protrusion configured for projecting into the first aperture of the bone screw, and the second spring tab secured to the second leg and including a second protrusion configured for projecting into the second aperture of the bone screw when the spring tab protrusions are biased toward respective bone screw apertures.

14. The guide member of claim 13 the bone screw attachment end further comprising an abutment surface disposed perpendicular to an axis of rotation of the guide member and configured for abutment with a top of the bone screw; the first and second legs each having an opening sized and shaped to allow passage of the protrusions into respective apertures in the bone screw; and including a sleeve that is slidingly mounted on the guide member and having a lower end that extends over the spring tabs so as to bias the protrusions into respective bone screw apertures as the sleeve slides axially downward relative to the guide member.

15. In a guide member having an elongate body with attachment structure at a lower end thereof and adapted to be secured to a bone screw implant; the improvement comprising:
a) a first laterally opening channel defining surface extending into an interior of the body and extending from a top end of the body to a bottom end thereof; and
b) a handle configured for releasable attachment to the guide member, the handle having a second laterally opening channel defining surface configured for coaxial alignment with the first laterally opening channel defining surface, the second laterally opening channel defining surface configured for receiving a manipulation tool and bone screw implant components therein.

16. In the combination of a bone screw having a head and a guide member having a bone screw attachment structure at a lower end thereof that is operably mateable with the bone screw head, the improvement comprising:
a) the bone screw head having first and second opposed apertures; and
b) the guide member lower end having first and second opposed spring tabs, each of the spring tabs having a top portion and a bottom portion and being biased radially outwardly away from an exterior of the guide member and away from the first and second opposed apertures; wherein
c) the top portion of each spring tab is attached to the guide member; and d) the bottom portion of each spring tab has a radially inwardly extending projection sized, shaped and positioned for insertion into one of the first and second opposed apertures.

17. The combination according to claim 16 wherein:
a) the projections extend radially inwardly into the apertures upon application of a downward force on the spring tab.

18. A spinal rod implantation tool assembly comprising:
a) an elongate guide member having an end configured for releaseable attachment to a spinal implant and a first channel defining surface having a first lateral opening along a substantial length of the guide member;
b) an elongate installation tool having a translation member and an attached sleeve, the translation member coaxial and being freely rotatable with respect to the sleeve, the translation member configured for rotatable attachment to the guide member, the sleeve having a rod pushing end, the rod pushing end translatable along the guide member and configured for pressing the guide member end into engagement with the spinal implant and for contact with and translation of a rod toward the spinal implant; and
c) a handle configured for releasable attachment to the guide member, the handle having a second channel defining surface configured for coaxial alignment with the first channel defining surface, and a second lateral opening configured for coaxial alignment with the first lateral opening, the second lateral opening configured for receiving a manipulation tool.

19. A spinal rod implantation tool assembly comprising:
a) a guide member including an elongate body with
I) an axial bore defining surface with an elongate lateral opening communicating with the bore defining surface;
ii) a first surface with a first guide and advancement structure thereon; and
iii) a bone screw attachment end adapted for releasable attachment to a bone screw and having first and second legs defining in part the elongate lateral opening and also defining a second lateral opening opposed to the elongate lateral opening, each of the legs including a leg aperture in a lower portion thereof; and
iv) first and second opposed spring tabs having a protrusion configured for projecting through one of the leg apertures and into an aperture of a bone screw attached to the bone screw attachment end, the first spring tab being attached to the first leg so as to bias the associated protrusion away from an associated bone screw aperture, and the second spring tab being attached to the second leg so as to bias the associated protrusion away from an associated bone screw aperture; and
b) an elongate installation tool assembly including a sleeve with
I) a second surface with a second guide and advancement structure thereon and mateable with the first guide and advancement structure; and
ii) a rod pushing end configured for pressing radially inwardly against the spring tabs and thereby projecting the protrusions through the leg apertures and into the bone screw apertures, the rod pressing end also configured for contact with and translation of a rod toward the bone screw.

20. An elongate guide tool having a handle structure at an end thereof and opposed implant engaging structure at an opposite end thereof, the guide tool having an axial channel defining surface with a lateral opening that extends a substantial length of the guide tool and includes a width sufficient to receive a rod therein, the channel being sized and shaped for side loading and receiving an implant fastener into a loading location positioned along the length of the channel.

21. A guide member for use with a spinal implant bone screw with a side aperture and an associated rod, the guide member comprising:
 a) an elongate body having an inner surface defining an elongate channel, the body further defining an elongate lateral opening communicating with the channel; and
 b) a bone screw attachment end having
  I) first and second legs defining in part the lateral opening; and
  ii) a spring tab cooperating with the first leg; a protrusion aligned and configured for projecting into the aperture of the bone screw when the bone screw and guide member are joined; the spring tab being outwardly biased to urge the protrusion away from the body.

22. The guide member of claim 21, the bone screw attachment end further comprising an abutment surface disposed perpendicular to an axis of rotation of the guide member and configured for abutment with a top of the bone screw; the first and second legs each having an opening sized and shaped to allow passage of the protrusions into the bone screw aperture; and including a sleeve that is slidingly mounted on the guide member and having a lower end that extends over the spring tab so as to bias the protrusion into the bone screw aperture as the sleeve slides axially downward relative to the guide member.

23. A guide member for use with a spinal implant bone screw with a side aperture and an associated rod, the guide member comprising:
 a) an elongate body having an inner surface defining an elongate channel, the body further defining a first elongate lateral opening communicating with the channel and extending an entire length of the elongate body; and
 b) a bone screw attachment end having
  I) first and second legs defining in part the first lateral opening; and
  ii) a spring-like flexible portion cooperating with the first leg and including a protrusion configured for projecting into the aperture of the bone screw, the spring-like flexible portion being outwardly biased to urge the protrusion away from the body.

24. The guide member of claim 23 the bone screw attachment end further comprising an abutment surface disposed perpendicular to an axis of rotation of the guide member and configured for abutment with a top of the bone screw; the first and second legs each having an opening sized and shaped to allow passage of the protrusions into the bone screw aperture; and including a sleeve that is slidingly mounted on the guide member and having a lower end that extends over the spring-like flexible portion so as to bias the protrusion into the bone screw aperture as the sleeve slides axially downward relative to the guide member.

25. A guide tool member for use with a spinal implant bone anchor with a side aperture and an associated rod, the guide tool member comprising:
 a) an elongate body having a longitudinal axis and an inner surface defining an elongate central bore about the axis, the body further defining an elongate lateral channel extending a length of the elongate body and communicating with the central bore, the channel aligned with a rod receiving channel in the bone anchor; and
 b) a bone anchor attachment end having
  I) first and second opposed legs defining in part the lateral channel; and
  ii) one of the first and second legs having a spring-like flexible portion including a protrusion configured for projecting into the aperture of the bone anchor and engaging the bone anchor.

26. A guide member for use with a spinal implant bone screw with first and second side apertures and an associated rod, the guide member comprising:
 a) an elongate body having an inner surface defining an elongate central bore, the body further defining an elongate lateral channel opening extending a length of the elongate body and communicating with the central bore; and
 b) a bone screw attachment at a lower end thereof, the bone screw attachment having
  I) first and second legs defining in part the lower end lateral channel opening; and
  ii) first and second opposed resilient extensions, the first extension cooperating with the first leg and including a first protrusion configured for projecting into the first aperture of the bone screw, and the second extension cooperating with the second leg and including a second protrusion configured for projecting into the second aperture of the bone screw when the protrusions are initially biased away from the first and second apertures and are pushed toward respective bone screw apertures by a structural member that translates along the elongate body.

27. The guide member of claim 26, wherein as the structural member translates along the elongate body, the structural member reduces a rod received in the elongate central opening downwardly toward an engaged bone screw.

28. A spinal rod implantation tool assembly comprising:
 a) an elongate guide member having a lower resilient end configured for releasable attachment to a spinal implant the implant having a receiver with a rod-receiving channel defining surface; the guide member having a guide member channel defining surface with a lateral opening along a substantial length of the guide member; the receiver channel defining surface and the guide member channel defining surface being alignable;
 b) an elongate installation tool having a translation member and an attached sleeve, the translation member coaxial and being freely rotatable with respect to the sleeve, the translation member configured for rotatable attachment to the guide member, the sleeve having a rod pushing end, the rod pushing end translatable along the guide member and configured for first pressing the guide member lower resilient end into engagement with the spinal implant and then for pushing and translating the rod toward and into the spinal implant receiver channel.

29. A tool assembly for inserting a spinal rod in a patient, the tool assembly comprising:
 a) a first elongate tool member having a central bore and opposed gripping lower end members that are biased outwardly with respect to each other and to an outer surface of the first elongate tool member and are adapted to grip a bone anchor when moved toward each other; and
 b) a second tool member configured for non-rotational translation along the first tool member and the lower end portions; wherein
 c) translation downward of the second tool member attaches the gripping lower end portions to a bone anchor and translation upward releases the gripping lower end portions from a bone anchor.

30. An elongate guide tool comprising:
a) a handle structure at a first end of a guide member;
b) an opposed implant engaging structure at a second end of the guide member; and
c) a channel defining surface extending from the first end to the second end and having a lateral opening wide enough to receive the width of a rod therein and that extends upward from a bottom of the guide member, the lateral opening being sized and shaped for side loading and receiving of an implant fastener into a loading location positioned along the length of the channel.

31. A guide tool assembly for use with a spinal implant bone screw, the screw having a head with first and second side apertures, and an associated rod, the guide tool assembly comprising:
a) an elongate body having an inner axial bore defined by an internal surface and an elongate laterally opening channel defining surface extending an entire length thereof and communicating with the axial bore defining surface; and the body having a bone screw attachment with
  I) first and second downwardly extending legs defining in part the laterally opening channel; and
  ii) the legs including inwardly projecting structures that are biased outwardly away from the body and the bone screw first and second apertures; and wherein
b) an outer sleeve is operative to cause the projecting structures to be biased into the apertures and the rod to be translated downwardly toward the screw head.

32. An elongate guide tool comprising:
a) a handle structure near a first end of the guide tool;
b) an opposed implant engaging structure near a second end of the guide tool; and
c) a channel defining surface extending between the first end and the second end and having a lateral opening with a lower portion wide enough to receive the width of a rod therein and extends the entire length of the guide tool, the lateral opening being sized and shaped for side loading and receiving an implant fastener into a loading location positioned along a length of the channel defining surface.

33. A guide member for use with a spinal implant bone screw with first and second side apertures and an associated rod, the guide member comprising:
a) an elongate body having an inner surface defining an elongate channel, the body further defining a first elongate lateral opening communicating with the channel; and
b) a bone screw attachment end having
  I) first and second legs defining in part the first lateral opening; and
  ii) first and second opposed spring tabs, the first spring tab secured to the first leg and including a first protrusion configured for projecting into the first aperture of the bone screw, and the second spring tab secured to the second leg and including a second protrusion configured for projecting into the second aperture of the bone screw when the spring tab protrusions are biased toward respective bone screw apertures; and
c) an outer surface having a first guide and advancement structure thereon adapted to rotatably and matingly receive a second guide and advancement structure disposed on a nut attachment of a rod pusher wherein rotation of the nut results in axial translation of the rod pusher with respect to the guide member.

34. In the combination of a bone screw having a head and a guide member having attachment structure at a lower end thereof that is operably mateable with the bone screw head; the improvement comprising:
a) the bone screw head having first and second opposed apertures; and
b) the guide member lower end having first and second opposed spring tabs, each of the spring tabs having a top portion and a bottom portion and being biased radially outwardly; wherein
c) the top portion of each spring tab is attached to the guide member; and
d) the bottom portion of each spring tab has a radially inwardly extending projection sized, shaped and positioned for insertion into one of the first and second opposed apertures; and
e) an elongate installation tool having a translation nut and an attached sleeve, the translation nut coaxial and being freely rotatable with respect to the sleeve, the nut configured for rotatable attachment to the guide member, the sleeve having a rod pushing end, the rod pushing end translatable along the guide member and onto the spring tab top portions, pressing the spring tab projections into the bone screw apertures.

35. A guide member for use with a spinal implant bone screw with a side aperture and an associated rod, the guide member comprising:
a) an elongate body having an inner surface defining an elongate channel, the body further defining a first elongate lateral opening communicating with the channel; and
b) a bone screw attachment end having
  I) first and second legs defining in part the first lateral opening; and
  ii) a spring protrusion cooperating with one of the first and second legs, aligned and configured for projecting into the aperture of the bone screw when the bone screw and guide member are joined; the spring being outwardly biased at the protrusion to urge the protrusion away from the body; and
c) an outer surface having a first guide and advancement structure thereon adapted to rotatably and matingly receive a second guide and advancement structure disposed on a nut attachment of a rod pusher wherein rotation of the nut results in axial translation of the rod pusher with respect to the guide member.

36. A guide member for use with a spinal implant bone screw with a side aperture and an associated rod, the guide member comprising:
a) an elongate body having an inner surface defining an elongate channel, the body further defining a first elongate lateral opening communicating with the channel; and
b) a bone screw attachment end having
  I) first and second legs defining in part the first lateral opening; and
  ii) a spring protrusion cooperating with one of the first and second legs, aligned and configured for projecting into the aperture of the bone screw when the bone screw and guide member are joined; the spring being outwardly biased at the protrusion to urge the protrusion away from the body; and
c) an upper portion defining a guide member opening for receiving a spring-loaded pin of a handle.

37. A guide member for use with a spinal implant bone screw with a side aperture and an associated rod, the guide member comprising:
   a) an elongate body having an inner surface defining an elongate channel, the body further defining a first elongate lateral opening communicating with the channel; and
   b) a bone screw attachment end having
      I) first and second legs defining in part the first lateral opening; and
      ii) a spring-like flexible portion cooperating with one of the first and second legs and including a protrusion configured for projecting into the aperture of the bone screw; and
   c) an outer surface having a first guide and advancement structure thereon adapted to rotatably and matingly receive a second guide and advancement structure disposed on a nut attachment of a rod pusher wherein rotation of the nut results in axial translation of the rod pusher with respect to the guide member.

38. A guide member for use with a spinal implant bone screw with a side aperture and an associated rod, the guide member comprising:
   a) an elongate body having an inner surface defining an elongate channel, the body further defining a first elongate lateral opening communicating with the channel; and
   b) a bone screw attachment end having
      I) first and second legs defining in part the first lateral opening; and
      ii) a spring-like flexible portion cooperating with one of the first and second legs and including a protrusion configured for projecting into the aperture of the bone screw; and
   c) an upper portion defining a guide member opening for receiving a spring-loaded pin of a handle.

39. A tool assembly adapted for use in implanting a spinal implant including a bone anchor and a rod in a patient comprising:
   a) an elongate guide member having an axis; the guide member having an upper end and a lower end for operably engaging the bone anchor during use; the guide member also having a channel sized and shaped to receive the rod;
   b) the guide member having a first spring tab at the lower end thereof that includes a projection that extends radially inward; the first spring tab projection being sized and shaped to be received in a slot in the bone anchor when aligned therewith and then biased radially inward;
   c) a second spring tab diametrically opposed to the first spring tab;
   d) a sleeve including a lower portion and an upper portion that rotates relative to the lower positions, and the sleeve upper portion is joined with the guide member by a helically wound guide rod advancement structure, such that rotation of the sleeve upper portion axially moves the sleeve relative to the guide member; the sleeve located on an exterior of the guide member and being axially moveable therealong; the sleeve having a bottom that openably engages the rod when the sleeve is urged downwardly and the rod is located in the channel; the sleeve also engaging the spring tabs so as to bias the spring tabs radially inwardly when the sleeve is advanced downward so as to urge the spring tab projections into the bone anchor slot when aligned therewith, such that the sleeve both urges the projection into the slot to secure the assembly to the bone anchor while urging the rod, when the rod is in the channel into the bone anchor.

40. A guide member for use with a spinal implant bone screw with first and second side apertures and an associated rod, the guide member comprising:
   a) an elongate body having an inner surface defining an elongate channel, the body further defining a first elongate lateral opening communicating with the channel; and
   b) a bone screw attachment end having
      I) first and second legs defining in part the first lateral opening; and
      ii) first and second opposed spring tabs, the first spring tab secured to the first leg and including a first protrusion configured for projecting into the first aperture of the bone screw, and the second spring tab secured to the second leg and including a second protrusion configured for projecting into the second aperture of the bone screw when the spring tab protrusions are biased toward respective bone screw apertures; and
   c) an upper portion defining an aperture for receiving a spring-loaded pin of a handle.

41. A tool assembly adapted for use in implanting a spinal implant including a bone anchor and a rod in a patient comprising:
   a) an elongate guide member having an axis; the guide member having an upper end and a lower end for operably engaging the bone anchor during use; the guide member also having a channel extending from the upper end to the lower end and sized and shaped to receive the rod;
   b) the guide member lower end having flexible members that extend outwardly away from an exterior of the guide member; each flexible member having an inward projecting structure, each of the projecting structures being sized and shaped to be received in a respective slot in the bone anchor when aligned therewith and then biased inwardly; and
   c) a sleeve located on the exterior of the guide member and being axially moveable therealong; the sleeve having a bottom that engages the rod when the sleeve is urged downwardly and the rod is located in the channel; the sleeve also engaging the flexible members so as to bias the members inwardly when the sleeve is advanced downward so as to urge the projecting structure into the bone anchor slot when aligned therewith, such that the sleeve both urges the projection into the slot to secure the assembly to the bone anchor while urging the rod, when the rod is in the channel into the bone anchor.

42. A spinal rod implantation tool assembly comprising:
   a) an elongate guide member having a body with a lower end configured for releaseable attachment to a spinal implant by resilient opposed implant engaging members and a channel defining surface having an opening along a lower portion of the guide member, the guide member channel defining surface aligning with a rod receiving channel defining surface in a receiver of the spinal implant, the resilient members sloping outwardly away from the guide member body;
   b) an elongate installation tool having a translation member and an attached sleeve, the translation member coaxial and being freely rotatable with respect to the sleeve, the translation member configured for rotatable attachment to the guide member, the sleeve having a rod pushing end, the rod pushing end translatable along the guide member and configured for pressing the guide member lower end resilient members inwardly into engagement with the spinal implant and for contact with and translation of a rod toward the spinal implant receiver channel.

\* \* \* \* \*